(12) United States Patent
Varanasi et al.

(10) Patent No.: US 11,697,671 B2
(45) Date of Patent: Jul. 11, 2023

(54) ENHANCED CRYSTAL NUCLEATION

(71) Applicant: Massachusetts Institute of Technology, Cambridge, MA (US)

(72) Inventors: Kripa K. Varanasi, Lexington, MA (US); Henri-Louis Girard, Somerville, MA (US); Caroline McCue, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 322 days.

(21) Appl. No.: 17/071,684

(22) Filed: Oct. 15, 2020

(65) Prior Publication Data

US 2021/0107936 A1   Apr. 15, 2021

Related U.S. Application Data

(60) Provisional application No. 62/915,111, filed on Oct. 15, 2019.

(51) Int. Cl.
| | |
|---|---|
| *C30B 7/02* | (2006.01) |
| *C07K 1/30* | (2006.01) |
| *C12N 9/36* | (2006.01) |
| *C30B 27/00* | (2006.01) |
| *G01N 33/00* | (2006.01) |

(52) U.S. Cl.
CPC ............ *C07K 1/306* (2013.01); *C12N 9/2462* (2013.01); *C12Y 302/01017* (2013.01); *C30B 7/02* (2013.01); *C30B 27/00* (2013.01); *G01N 2033/0003* (2013.01)

(58) Field of Classification Search
CPC .......... C30B 7/02; C30B 27/00; C30B 29/58; C07K 1/306; C12N 9/2463; G01N 2033/0003
See application file for complete search history.

(56) References Cited

U.S. PATENT DOCUMENTS

2006/0003931 A1\*   1/2006   Eigenbrot, Jr. .... C07K 14/4753
                                                                  702/19

FOREIGN PATENT DOCUMENTS

| CA | 2624965 | \* | 4/2007 |
| EP | WO2005/067956 | \* | 7/2005 |

OTHER PUBLICATIONS

Artusio et al., Surface-induced crystallization of pharmaceuticals and biopharmaceuticals: A review. Int J Pharm. Aug. 25, 2018;547(1-2):190-208. doi: 10.1016/j.ijpharm.2018.05.069. Epub May 31, 2018.
Asanithi et al., Carbon-nanotube-based materials for protein crystallization. ACS Appl Mater Interfaces. Jun. 2009;1(6):1203-10.
Brange et al., Insulin analogs with improved pharmacokinetic profiles. Adv Drug Deliv Rev. Feb. 1, 1999;35(2-3):307-335. Epub Jan. 22, 1999.
Chayen et al., Porous silicon: an effective nucleation-inducing material for protein crystallization. J. Mol. Biol. Sep. 28, 2001;312(4):591-595.

(Continued)

*Primary Examiner* — Robert M Kunemund
(74) *Attorney, Agent, or Firm* — Wolf, Greenfield & Sacks, P.C.

(57) ABSTRACT

Crystal nucleation, and associated articles, systems, and methods, are generally described.

16 Claims, 27 Drawing Sheets

(56) References Cited

OTHER PUBLICATIONS

Chen et al., Nanodiamonds as Nucleating Agents for Protein Crystallization. Langmuir. Jul. 5, 2017;33(26):6521-6527. Epub Jun. 21, 2017.

Delmas et al., Nucleation and crystallization of lysozyme: role of substrate surface chemistry and topography. J. Adhes. Sci. Technol. 2011;25(4-5):357-366. Epub Apr. 2, 2012.

Drake et al., An emerging playbook for antibody-drug conjugates: lessons from the laboratory and clinic suggest a strategy for improving efficacy and safety. Curr Opin Chem Biol. Oct. 2015;28:174-80. Epub Sep. 2, 2015.

Ecker et al., The therapeutic monoclonal antibody market. MAbs. 2015;7(1):9-14. Epub Dec. 20, 2014.

Elgundi et al., The state-of-play and future of antibody therapeutics. Adv Drug Deliv Rev. Dec. 1, 2017;122:2-19. Epub Dec. 2, 2016.

Fermani et al., Protein crystallization on polymeric film surfaces. Journal of Crystal Growth. Apr. 2001;224:327-34.

Govada et al., Exploring carbon nanomaterial diversity for nucleation of protein crystals. Sci. Rep. Feb. 4, 2016;6:20053. 11 pages.

Gully et al., Colloidal graphenes as heterogeneous additives to enhance protein crystal yield. Nanoscale. Sep. 7, 2012;4(17):5321-4. doi: 10.1039/c2nr31150j. Epub Jul. 26, 2012.

Guo et al., Utilisation of adsorption and desorption for simultaneously improving protein crystallisation success rate and crystal quality. Sci Rep. Dec. 4, 2014;4:7308. 8 pages, doi: 10.1038/srep07308.

Hekmat et al., Crystallization of lysozyme: From vapor diffusion experiments to batch crystallization in agitated ml-scale vessels. Process Biochemistry. 2007;42:1649-54. Epub Oct. 13, 2007.

Hodzhaoglu et al., Gold nanoparticles induce protein crystallization. Crystal Research and Technology. 2008;43(6):588-93. Epub May 5, 2008.

Holtze et al.., Biocompatible surfactants for water-in-fluorocarbon emulsions. Lab on a Chip. 2008;8:1632-9. Epub Sep. 2, 2008.

Kertis et al., Heterogeneous nucleation of protein crystals using nanoporous gold nucleants. J. Mater. Chem. Aug. 31, 2012;22(41):21928-21934.

Khurshid et al., Porous nucleating agents for protein crystallization. Nat Protoc. Jul. 2014;9(7):1621-33. doi: 10.1038/nprot.2014.109. Epub Jun. 12, 2014.

Koizumi et al., Control of Nucleation Rate for Tetragonal Hen-Egg White Lysozyme Crystals by Application of an Electric Field with Variable Frequencies. Crystal Growth & Design. 2009;9(5):2420-4. Epub Mar. 2, 2009.

Kontermann et al., Bispecific Antibodies. Drug Discov Today. Jul. 2015;20(7):838-47.

Rathore et al., Continuous processing for production of biopharmaceuticals. Prep Biochem Biotechnol. 2015;45(8):836-49. Epub Feb. 12, 2015.

Ribeiro et al., Use of Gold Nanoparticles as Additives in Protein Crystallization. Crystal Growth & Design. 2014;14:222-7. Epub Nov. 13, 2013.

Saridakis et al., Protein crystallization facilitated by molecularly imprinted polymers. PNAS. Jul. 2011;108(27):11081-6. Erratum included. PNAS. Nov. 2011;108(45):18566.

Sazaki et al., Novel coupling effects of the magnetic and electric fields on protein crystallization. Journal of Crystal Growth. Feb. 2004;262:499-502.

Sögütoglu et al., Viedma ripening: a reliable crystallisation method to reach single chirality. Chem. Soc. Rev. 2015;44:6723-32. Epub Jul. 13, 2015.

Weichsel et al., Enhanced nucleation of lysozyme using inorganic silica seed particles of different sizes. Cryst. Growth Des. Jun. 17, 2015;15(8):3582-3593.

Yang et al., Crystalline monoclonal antibodies for subcutaneous delivery. PNAS. Jun. 10, 2003;100(12):6934-9.

Akella, et al. "Emulsion-Based Technique to Measure Protein Crystal Nucleation Rates of Lysozyme," *Cryst. Growth Des.* 14, pp. 4487-4509. Jul. 28, 2014.

* cited by examiner

ENHANCED CRYSTAL NUCLEATION

RELATED APPLICATIONS

This application claims priority under 35 U.S.C. § 119 (e) to U.S. Provisional Patent Application No. 62/915,111, filed Oct. 15, 2019, and entitled "Enhanced Crystal Nucleation," which is incorporated herein by reference in its entirety for all purposes.

TECHNICAL FIELD

Crystal nucleation, and associated articles, systems, and methods, are generally described.

SUMMARY

Articles, systems, and methods related to crystal nucleation are generally disclosed. The subject matter of the present invention involves, in some cases, interrelated products, alternative solutions to a particular problem, and/or a plurality of different uses of one or more systems and/or articles.

Certain aspects are related to composite structures. In some embodiments, the composite structure comprises a particle, and a plurality of selective binding agents bound to an external surface of the particle, wherein the areal density of the selective binding agents over the external surface of the particles is less than or equal to 100 per $nm^2$.

Some aspects are related to collections of composite structures. In some embodiments, at least some of the composite structures comprise a surface having an outer boundary, a plurality of selective binding agents proximate to the outer boundary, and crystalline material or a precursor thereof in contact with at least one of the selective binding agents.

In certain embodiments, at least some of the composite structures comprise a domain having an outer boundary, one or more agents proximate to the outer boundary, and crystalline material or a precursor thereof in contact with at least one of the one or more agents, wherein at least one of the one or more agents is configured to selectively bind the crystalline material or the precursor.

Certain aspects are related to crystallization systems. In some embodiments, the crystallization system comprises a liquid medium comprising a solubilized crystal precursor and a plurality of particles functionalized with one or more agents, wherein at least one of the one or more agents is configured to selectively bind to the solubilized crystal precursor, and wherein the crystallization system is capable of generating crystals comprising the solubilized crystal precursor when a concentration of the solubilized crystal precursor in the liquid medium is below a saturation concentration.

In certain aspects, methods are provided. In some embodiments, the method comprises combining a solubilized crystal precursor with a plurality of surfaces in a liquid medium, and generating a crystal comprising the solubilized crystal precursor, wherein at least some of the surfaces comprise one or more agents configured to selectively bind to the solubilized crystal precursor.

According to certain embodiments, a composite structure is described. In some embodiments, the composite structure comprises a surface and a plurality of selective binding agents bound to the surface. The areal density of the selective binding agents over the surface is less than or equal to 100 per $nm^2$, in certain embodiments.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
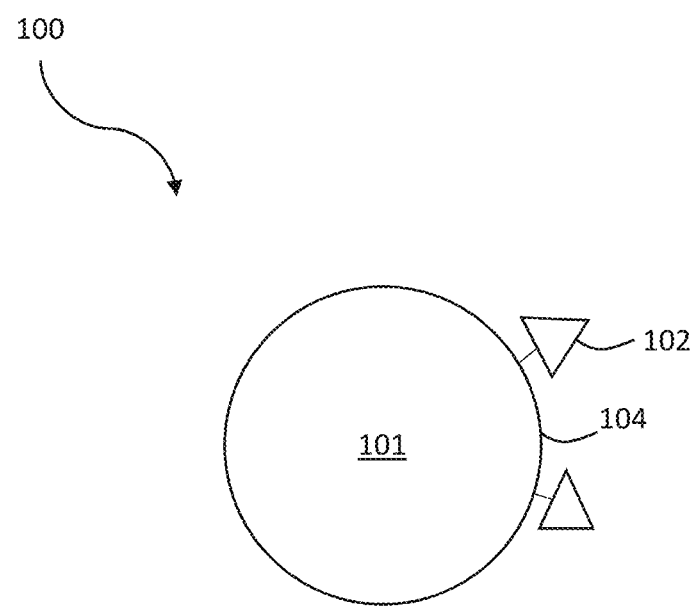
FIG. 1A is a schematic diagram of a local concentrator composite structure, according to one or more embodiments.

Articles, systems, and methods related to crystal nucleation are generally disclosed. In some embodiments, local concentrators are employed to enhance crystal nucleation. The local concentrators can be, in some embodiments, nanoscale (e.g., having a largest cross-sectional dimension of less than 1000 nm, less than 100 nm, or less than 10 nm) and/or microscale (e.g., having a largest cross-sectional dimension of from 1 micrometer to 1000 micrometers, from 1 micrometer to 100 micrometers, or from 1 micrometer to 10 micrometers) colloidal elements (e.g., particles, molecules, or liquid droplets) dispersed in a solution of crystallizable product. The local concentrators are designed, in some embodiments, to interact with the crystallizable product (e.g., via coulombic, van der Waals, covalent, or other interactions) in such a way as to increase the local concentration of the crystallizable product in their vicinity. In accordance with certain embodiments, the local concentrators can also interact with the crystallizable product in such a way as to align the particles and/or molecules of the crystallizable product with each other (e.g., alignment of dipole moments or site-specific interactions). In some embodiments, the local concentrators serve as heterogeneous nucleation sites for the crystallizable product. Through these interactions, the local concentrators can allow for the crystallization of the product in their vicinity at faster rates and lower concentrations than in a reference solution (e.g., a reference solution without the local concentrators but that is otherwise identical).

Certain embodiments are related to a framework to increase the nucleation rate of crystallizable particles that capitalizes on the study of that particle's interaction with interfaces. Through the use of local concentrators, the nucleation rate of such crystallizable particles can be significantly increased, for example, in comparison to a reference solution without the concentrators but that is otherwise identical. The specific characteristics of the concentrators can, in certain embodiments, be tuned to adjust the balance between nucleation and growth of crystals, allowing for the control of the characteristics of the produced crystals.

While embodiments are described primarily in the context of the crystallization of proteins, the articles, systems, and methods described herein are not so limited and can be applied to the crystallization of other agents such as small and large pharmaceuticals and other molecules, and other crystallizable materials/particles.

In conventional crystallization systems, surfaces in contact with a supersaturated protein solution cause heterogeneous nucleation to occur. The physio-chemical properties of the surface (such as charge, roughness, surface energy, and functional groups) affect the crystallization dynamics and the characteristics of the crystals obtained. The introduction of particles in a solution of crystallizable proteins has further been found to enable nucleation in so-called metastable conditions that would not otherwise have led to the nucleation of crystals.

In accordance with certain embodiments, and in contrast with conventional crystallization systems, particles are introduced that are specifically designed to attract and bind to proteins via different mechanisms (e.g., surface energy, charge interaction, or covalent interactions).

In some embodiments, a composite structure is described, wherein the composite structure comprises a particle. FIG. 1A is a schematic diagram of a local concentrator composite structure, according to one or more embodiments. As shown in FIG. 1A, composite structure 100 comprises particle 101. According to certain embodiments, the composite structure comprises a solid particle. In some embodiments, for example, the particle is a nanoparticle (e.g., a particle having a largest cross-sectional dimension of less than 1000 nanometers, such as from 10 nanometers to 1000 nanometers, from 10 nanometers to 100 nanometers, or from 100 nanometers to 1000 nanometers), a microparticle (e.g., a particle having a largest cross-sectional dimension of from 1000 nanometers to 1000 micrometers, or from 1000 nanometers to 100 micrometers), and/or a quantum dot. The particle may comprise, in certain embodiments, any of a variety of suitable materials. For example, in some embodiments, the particle comprises a metal (e.g., gold, silver), an oxide (e.g., silicon dioxide, graphene oxide, titanium oxide, iron oxide), a hydroxide (e.g., aluminum hydroxide), a lipid (e.g., lipid nanoparticles), and/or a polymer (e.g., polymeric nanoparticles), although other materials are possible.

In certain embodiments, and as shown in FIG. 1A, plurality of binding agents 102 are bound to external surface 104 of particle 101. Examples of selective binding agents include functional groups, charged moieties, and/or specific linkers, which may impart particle 101 with desirable surface properties. In some embodiments, for example, a person of ordinary skill in the art would be able to choose certain bioconjugates that can bind to target amino acids (e.g., on proteins) through known bioconjugation techniques. Non-limiting examples of common bioconjugation techniques include maleimide-thiol reactions and/or succinimidyl-amine reactions, although other bioconjugation techniques are possible and would be known to a person of ordinary skill in the art.

In some embodiments, exemplary functional groups include maleimide groups, N-hydroxysuccinimide ester groups, carboxylic acid groups, and/or amine groups, although other functional groups are also possible. Exemplary charged moieties include diazonium salts, in certain embodiments, although other charged moieties are possible. Non-limiting examples of specific linkers include biotin, isocyanates, isothiocyanates, and/or iodoacetamides.

The plurality of selective binding agents 102 may be bound to external surface 104 of particle 101 via any of a variety of suitable bonding mechanisms, including, but not limited to, covalent bonding, ionic bonding, van der Waals forces, and/or hydrogen bonding. In certain non-limiting embodiments, for example. wherein the selective binding agents are covalently bound to the external surface of the solid particles.

In certain non-limiting embodiments, the selective binding agents are capable of selectively binding to specific sites on a protein, as is described in further detail herein.

The areal density of the selective binding agents over the external surface of the particle may be any of a variety of suitable areal densities. As would be recognized by those of ordinary skill in the art, areal density in this context refers to a measure of the quantity of the selective binding agent per unit area of the particle. In certain embodiments, the areal density of the selective binding agents over the external surface of the particle is less than or equal to 100 per $nm^2$, less than or equal to 10 per $nm^2$, less than or equal to 1 per $nm^2$, less than or equal to 0.1 per $nm^2$, less than or equal to 0.01 per $nm^2$, or less. In certain embodiments, the areal density of the selective binding agents over the external surface of the particle is greater than or equal to 0.001 per $nm^2$, greater than or equal to 0.01 per $nm^2$, greater than or equal to 0.1 per $nm^2$, greater than or equal to 1 per $nm^2$, greater than or equal to 10 per $nm^2$, or more. Combinations of the above recited ranges are also possible (e.g., the areal density of the selective binding agents over the external surface of the particle is less than or equal to 100 per $nm^2$ and greater than or equal to 0.001 per $nm^2$, the areal density of the selective binding agents over the external surface of the particle is less than or equal to 10 per $nm^2$ and greater than or equal to 0.1 per $nm^2$). Other combinations are also possible.

Figure 1B:
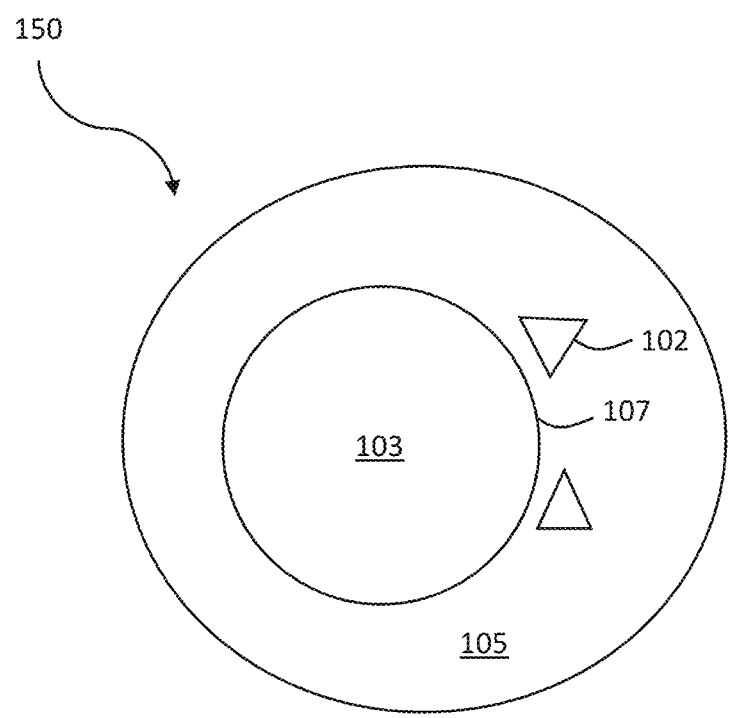
FIG. 1B is a schematic diagram of a local concentrator composite structure comprising an emulsified droplet, according to one or more embodiments.

In certain embodiments, the composite structure is located within a liquid medium. For example, in some embodiments the composite structure may be at least partially dispersed, suspended, and/or dissolved in a liquid medium. According to some embodiments, the composite structure may be at least partially dissolved in a first liquid that is dispersed in a second liquid in which the first liquid is not soluble or miscible (e.g., in an emulsion). FIG. 1B is a schematic diagram of a local concentrator composite structure comprising an emulsified droplet, according to one or more embodiments. As shown in FIG. 1B, composite structure 150 comprises emulsified droplet 103 dispersed in emulsifying liquid 103 (e.g., liquid in which the emulsified droplet is not soluble or miscible).

In embodiments in which emulsion droplets are employed, the droplet can have any of a variety of suitable dimensions. In some embodiments, the emulsion droplet is nanoscale (e.g., having a largest cross-sectional dimension of less than 1000 nanometers, such as from 10 nanometers to 1000 nanometers, from 10 nanometers to 100 nanometers, or from 100 nanometers to 1000 nanometers). In certain embodiments, the emulsion droplet is microscale (e.g., having a largest cross-sectional dimension of from 1000 nanometers to 1000 micrometers, or from 1000 nanometers to 100 micrometers).

According to some embodiments, composite structure 150 comprises selective binding agents 102. Composite structure 150 may, in certain embodiments, comprise selective binding agents 102 proximate to phase boundary 107 of emulsified droplet 103 (e.g., the phase boundary between the emulsified droplet and the emulsifying liquid in which the emulsified droplet is not soluble or miscible). In some embodiments, selective binding agents 102 are at least partially soluble in emulsifying liquid 103. For example, in certain non-limiting embodiments, the selective binding agent comprises a surfactant (e.g., a surfactant solubilized in the emulsifying liquid). The surfactant may, in certain embodiments, be proximate to phase boundary 107 of emulsified droplet 103.

Figure 1C:
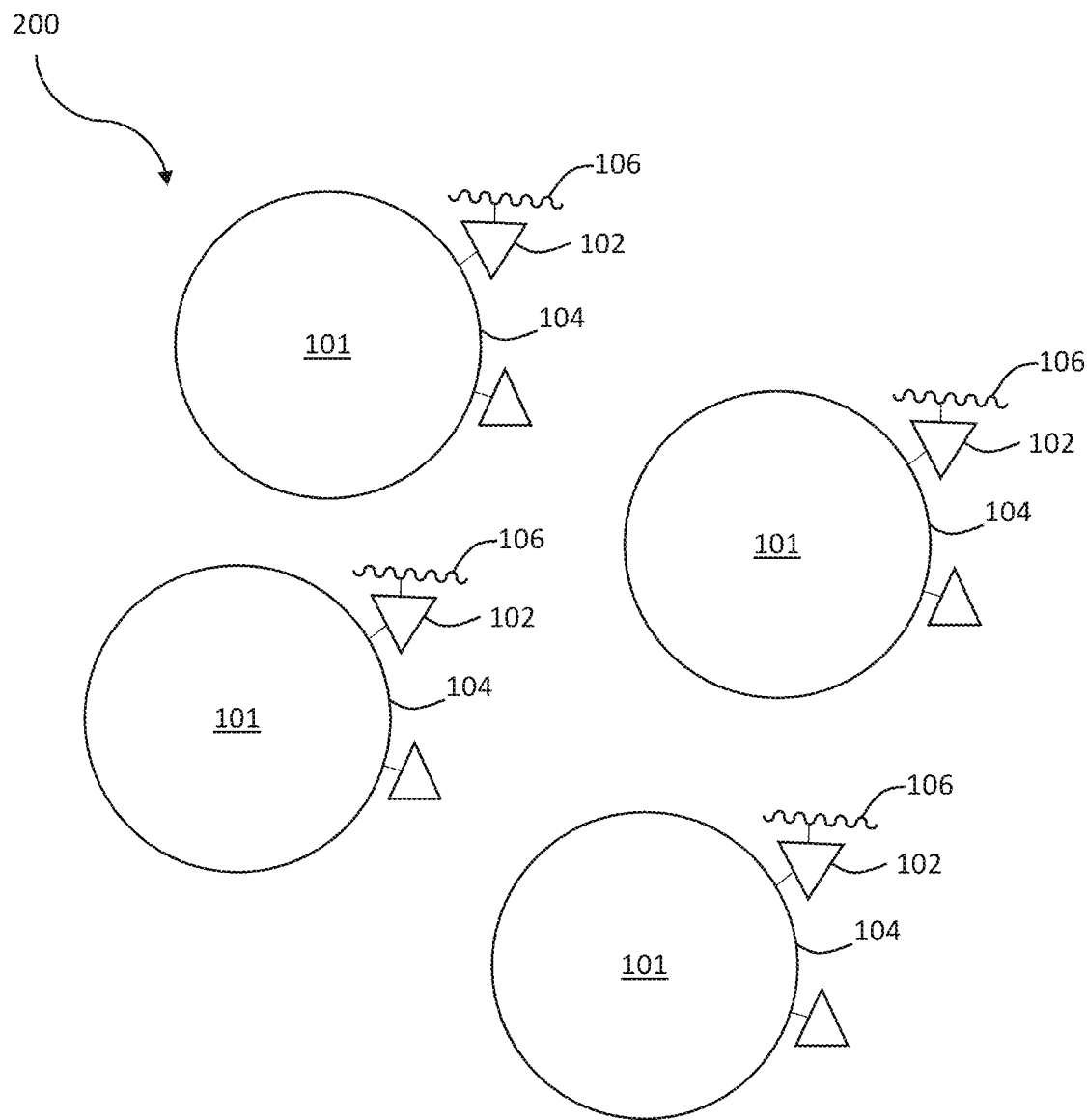
FIG. 1C is a schematic diagram of a first collection of local concentrator composite structures, according to one or more embodiments.

According to certain embodiments, a collection of composite structures is described. FIG. 1C is a schematic diagram of a first collection of local concentrator composite structures, according to one or more embodiments. As shown in FIG. 1C, collection of composite structures 200 comprises a plurality of particles 101. The collection of composite structures may comprise any of a variety of suitable amounts of particles (e.g., greater than or equal to 2 particles, greater than or equal to 100 particles, greater than or equal to 1,000 particles, greater than or equal to 10,000 particles, greater than or equal to 100,000 particles, greater than or equal to 1,000,000 particles or more).

In certain embodiments, the plurality of particles 101 comprise external surface 104 having an outer boundary. The plurality of particles 101, in some embodiments, comprise selective binding agents 102 proximate to the outer boundary of external surface 104. For example, in some embodiments, selective binding agents 102 may be bound (e.g., covalently bound) to the outer boundary of external surface 104.

According to some embodiments, the plurality of particles 101 comprise crystalline material 106, or a precursor thereof. Crystalline material 106, in some embodiments, is in contact with at least one selective binding agent 102. In certain non-limiting embodiments, for example, crystalline material 106 comprises a protein. The crystalline material may comprise insulin and/or an antibody (e.g., monoclonal antibodies), in some embodiments. Other crystalline materials are possible.

Figure 1D:
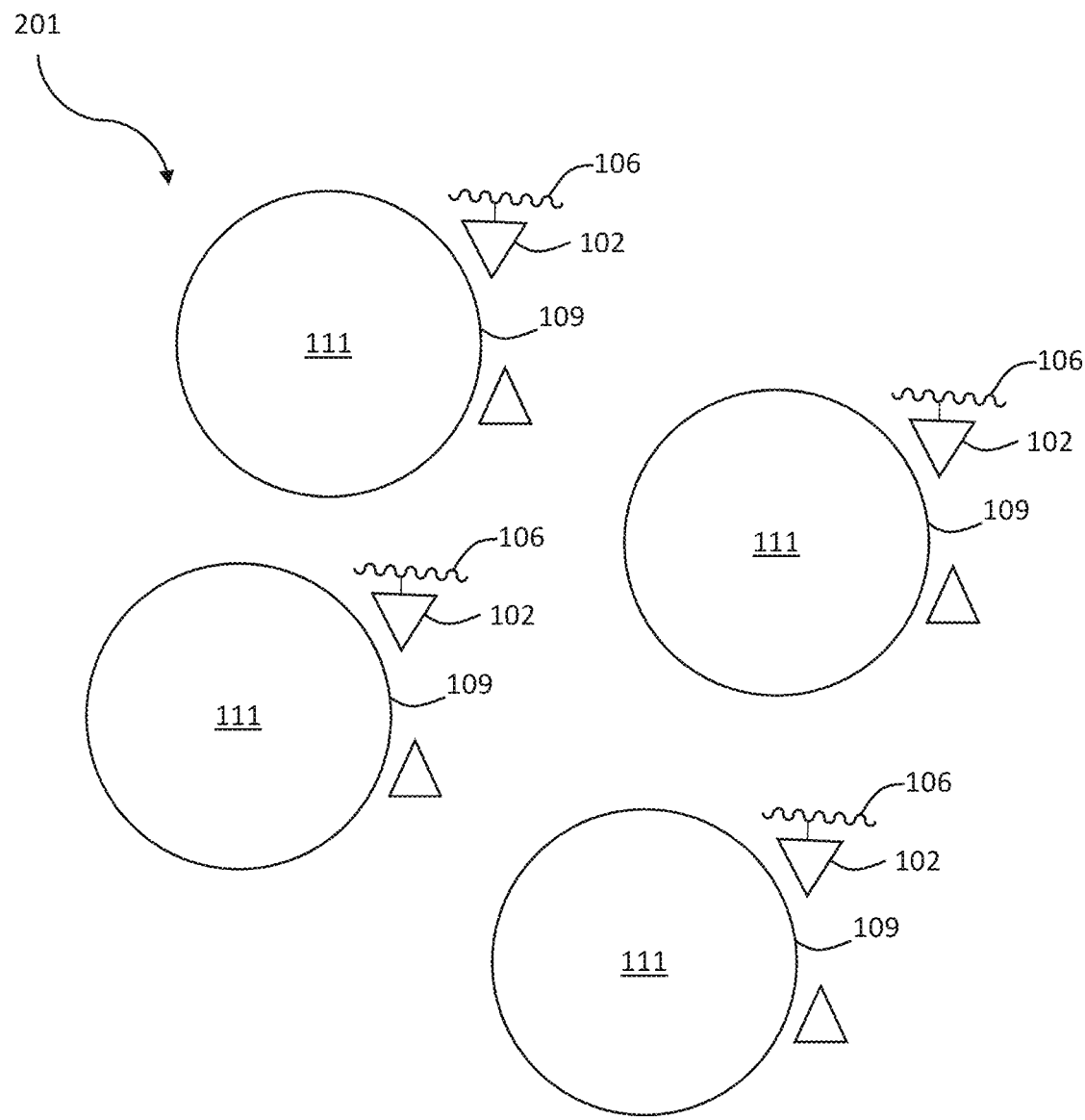
FIG. 1D is a schematic diagram of a second collection of local concentrator composite structures, according to one or more embodiments.

FIG. 1D is a schematic diagram of a second collection of local concentrator composite structures, according to one or more embodiments. As shown in FIG. 1D, collection of composite structures 201 comprises a plurality of domains 111 (e.g., particles, emulsified droplets).

According to certain embodiments, domains 111 have outer boundary 109. Collection of composite structures 201 comprise, in some embodiments, one or more agents 102 proximate to outer boundary 109. In certain embodiments, collection of composite structures 201 comprises crystalline material 106, or a precursor thereof, in contact with at least one of one or more agents 102.

Figure 1E:
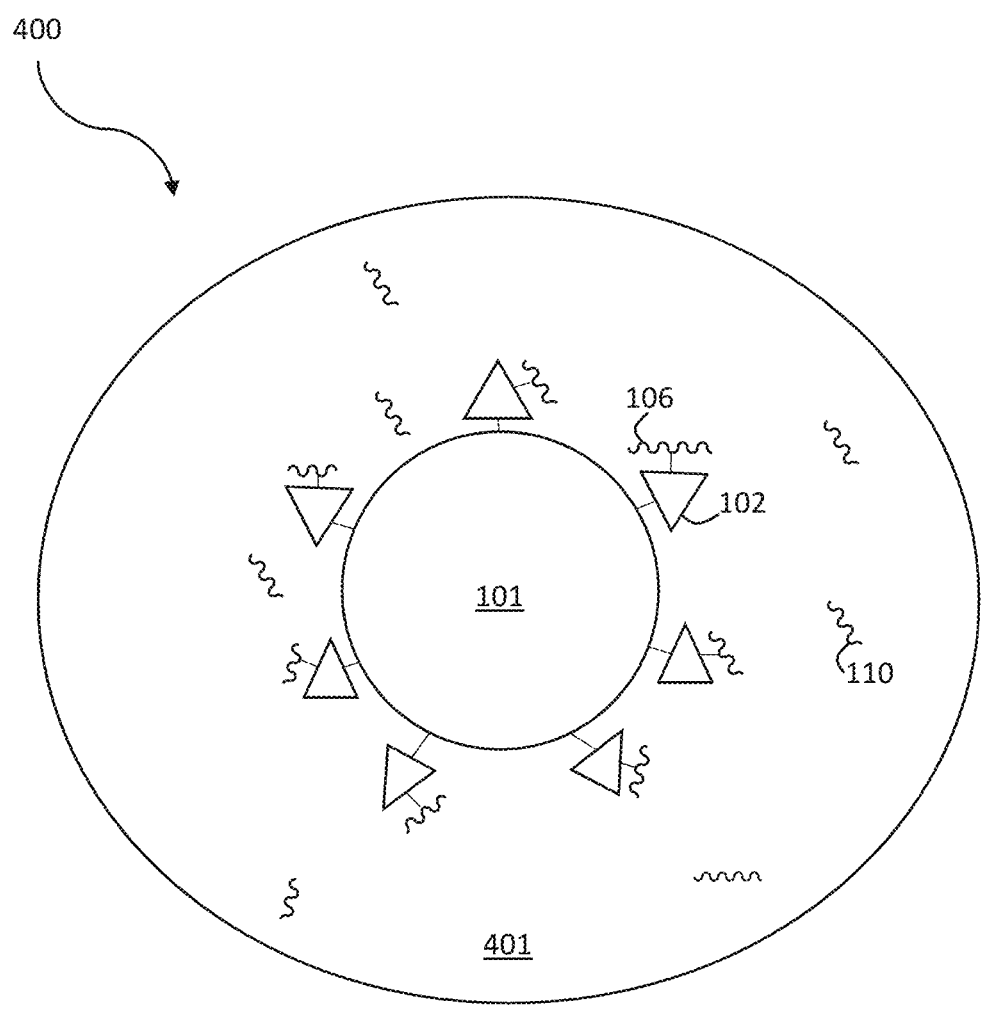
FIG. 1E is a schematic diagram of a crystallization system, according to one or more embodiments.

In some embodiments, at least one of one or more agents 102 is configured to selectively bind crystalline material 106. For example, in certain non-limiting embodiments, the selective binding agents are capable of selectively binding to specific sites on a crystalline material (e.g., protein). Generally, the selective binding agent selectively binds to the crystallizable material rather than other materials in the domain in which the local concentrator composite structure is present. According to certain embodiments, a crystallization system is described. FIG. 1E is a schematic diagram of a crystallization system, according to one or more embodiments. Crystallization system 400 comprises, in some embodiments, liquid medium 401 (e.g., protein solution). Liquid medium 401 comprises crystal precursor 110, in some embodiments. In some embodiments, crystal precursor 110 may be at least partially solubilized in liquid medium 401. For example, in certain non-limiting embodiments, crystal precursor 110 is a precursor of a crystallized protein.

According to certain embodiments, crystallization system comprises particle 101 functionalized with one or more agents 102. In some embodiments, at least one of one or more agents 102 is configured to selectively bind (e.g. covalently bind) to crystal precursor 110, thereby providing crystalline material 106. For example, one or more agents 102 may be configured to selectively bind to specific sites on a protein (e.g., amino acids). In some embodiments, crystallization system 400 is capable of generating crystals comprising solubilized crystal precursor 110 when a concentration of solubilized crystal precursor 110 in liquid medium 401 is below a saturation concentration. For example, in certain embodiments, a concentration of the solubilized crystal precursor within the liquid medium is less than or equal to 0.9, less than or equal to 0.8, less than or equal to 0.7, less than or equal to 0.6, less than or equal to 0.5, less than or equal to 0.4, less than or equal to 0.3, less than or equal to 0.2, or less than or equal to 0.1 times a saturation concentration of the solubilized crystal precursor within the liquid medium.

Figure 1F:
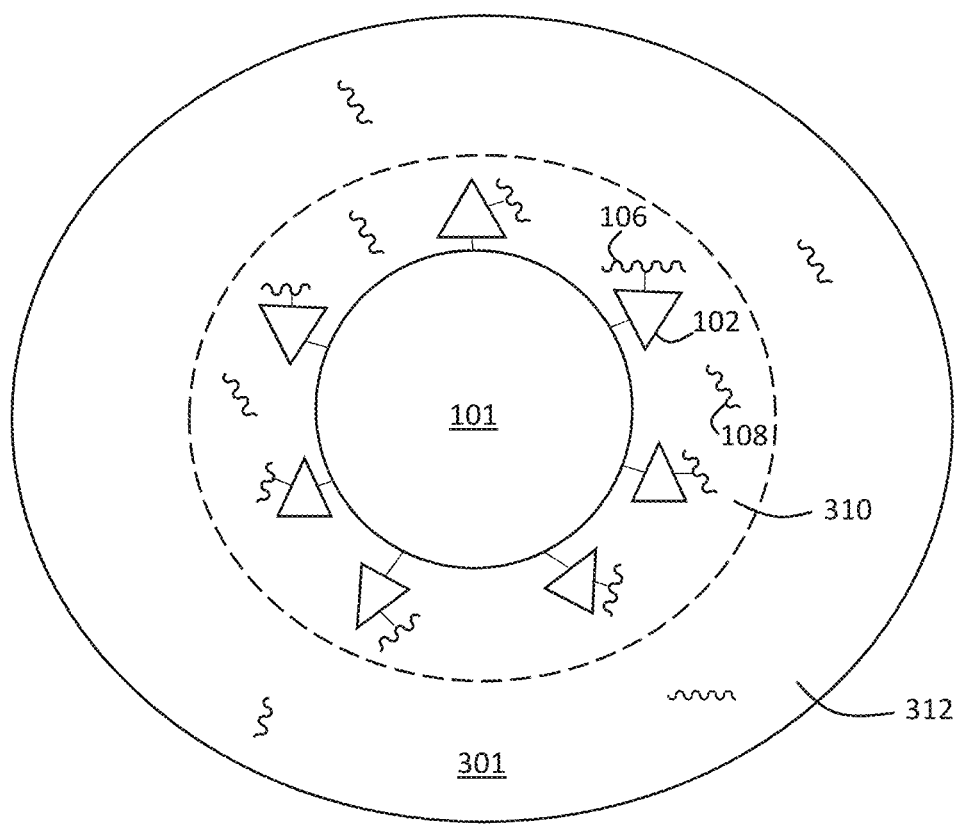
FIG. 1F is a schematic diagram of a local concentrator for increased crystal nucleation, according to one or more embodiments.

FIG. 1F is a schematic diagram a local concentrator for increased crystal nucleation, according to one or more embodiments. FIG. 1F, according to some embodiments, demonstrates a proposed mechanism for the use of local concentrators (e.g., domains such as solid particles, emulsified droplets, etc.) to increase nucleation rates. In some embodiments, the domains (e.g., particles, emulsified droplets, etc.), of nano- to micro-metric size, are dispersed in a protein solution. For example, referring to FIG. 1F, particle 101 may be dispersed in protein solution 301. While a particle is shown in FIG. 1F, other suitable domains could be used (e.g., emulsion droplets, etc.). In certain embodiments, agents (e.g., functional groups, charge, presence of specific linkers, etc. which may impart surface properties) interact with the proteins in such a way to increase the local protein concentration. For example, in some non-limiting embodiments, particles 101 (or other domains) can be functionalized with binding agents 102 (e.g., linker groups such as maleimides) that bind directly to specific portions of protein 108, such as amino acids or even linking sequences that could bind to short amino acid sequences, resulting in agent 102 bound to crystalline material 106. The similarity of interaction between identical proteins and the domain may also, in some embodiments, cause an alignment of the proteins with each other, for instance along their dipole axis or by binding with the particle at a specific site. This in turn yields, in accordance with certain embodiments, favorable nucleation conditions that produce crystals faster than in a bulk region devoid of particles. Referring to FIG. 1F, nucleation region 310 exhibits a higher concentration of protein 108, as compared to growth region 312, because of the attractive properties of particle 101.

In addition, the domains can be engineered to respond to an external field such as an electric field, illumination, or temperature gradients to activate all or some of their functionalities.

Figure 1G:
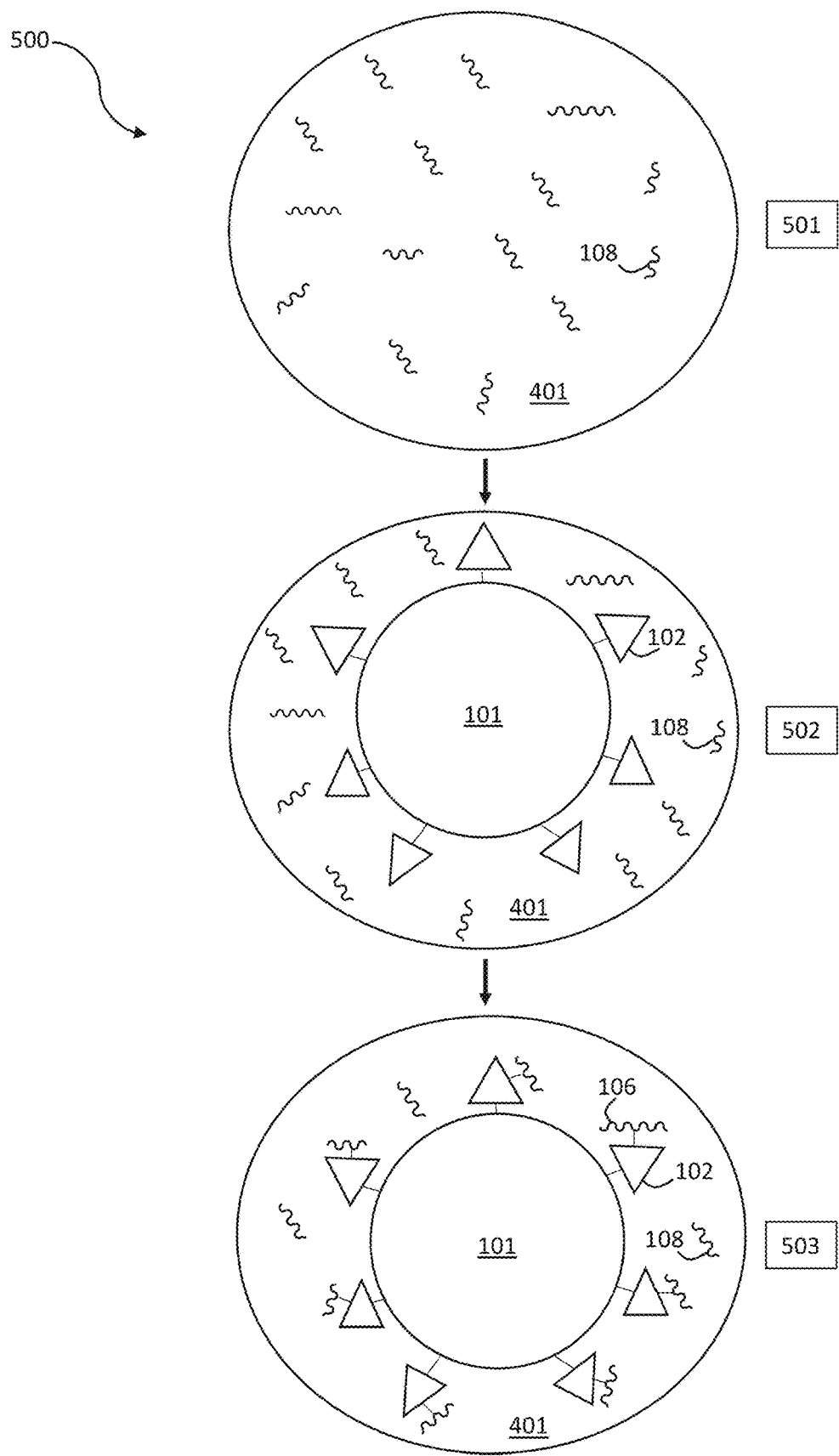
FIG. 1G is a schematic diagram depicting a method of generating a crystal, according to one or more embodiments.

According to certain embodiments, a method is described. FIG. 1G is a schematic diagram depicting a method of generating a crystal, according to one or more embodiments. In some embodiments, method 500 comprises providing liquid medium 401 comprising a solubilized precursor 108 (see, e.g., step 501). Method 500 further comprises, in certain embodiments, combining solubilized crystal precursor 108 with one or more surfaces (e.g., particles 101, emulsified droplets, etc.) in liquid medium 401 (see, e.g., step 502). According to some embodiments, method 500 further comprises generating crystalline material 106 comprising solubilized crystal precursor 108 (see, e.g., step 503).

Table 1 shows a list of non-limiting example particles used in the study of the effect of local concentrators on protein nucleation and their respective properties. In particular, particles of various charge, surface energy, and functional groups were used as well as particles functionalized with amino acid specific binding sites. The use of silica and gold nanoparticles as a base was motivated by their good availability, biocompatibility, and ease of functionalization. Graphene quantum dots allowed for the exploration of 1-10 nm particle sizes (close to the critical nucleation radius) and provided a platform for protein specific linker groups.

TABLE 1

Particles used for the study of the impact of local concentrators on protein crystallization and their characteristics.

| Type | Base | Functionality | # | Size (nm) | Charge (mV) @ pH 7 | Interaction with proteins |
|---|---|---|---|---|---|---|
| Nanoparticle | SiO$_2$ | / | 1 | 140 | | Surface |
| | | | 2 | 110 | −30 | energy |
| | | | 3 | 150 | −40 | Coulombic |
| | | | 4 | 150 | −51 | interactions |
| | | COOH | | 200 | −35 | |
| | Gold | / | | 300 | −50 | |
| Graphene quantum dots | Graphene oxide | / | 2 | 4-7 | | |
| | | | 3 | 8-10 | | |
| | | NHS-ester | 1 | 8-10 | | Surface |
| | | | 2 | 4-7 | | energy |
| | | | 3 | 1-4 | | Coulombic interactions Lysine binding |
| | | Maleimide | 1 | 8-10 | | Surface |
| | | | 2 | 4-7 | | energy |
| | | | 3 | 1-4 | | Coulombic interactions Cysteine binding |
| Aluminum Hydroxide precipitate | | | | | | Surface energy Coulombic interactions |

Figure 1H:
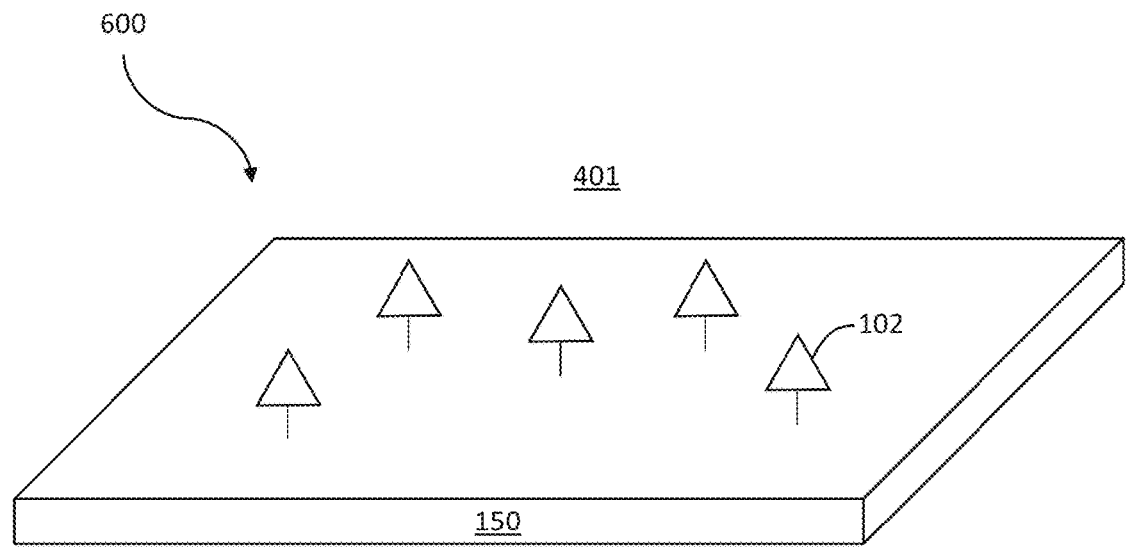
FIG. 1H is a schematic diagram of a local concentrator composite structure comprising a surface, according to one or more embodiments.

In some embodiments, a composite structure is described, wherein the composite structure comprises a surface. FIG. 1H is a schematic diagram of a local concentrator composite structure comprising a surface, according to one or more embodiments. As shown in FIG. 1H, composite structure 600 comprises surface 150. The surface may comprise any of the materials described herein with respect to the particle. For example, the surface may comprise a metal (e.g., gold, silver), an oxide (e.g., silicon dioxide, graphene oxide, titanium oxide, iron oxide), a hydroxide (e.g., aluminum hydroxide), a lipid, and/or a polymer, although other materials are possible.

Referring to FIG. 1H, plurality of selective binding agents 102 may be bound to surface 150, in some embodiments. Exemplary selective binding agents have been described herein, including, but not limited to, functional groups, charged moieties, and/or specific linkers. Plurality of selective binding agents 102 may be bound to surface 150 via any of a variety of bonding mechanisms, such as covalent bonding, ionic bonding, van der Waals forces, and/or hydrogen bonding. In some embodiments, plurality of selective binding agents 102 may be coated, deposited, and/or immobilized on surface 150 using techniques known to a person of ordinary skill in the art (e.g., spray coating, chemical vapor deposition, additive manufacturing, etc.). The areal density of the plurality of selective binding agents over the surface may be any of the areal densities described herein with respect to the particle.

Figure 1I:
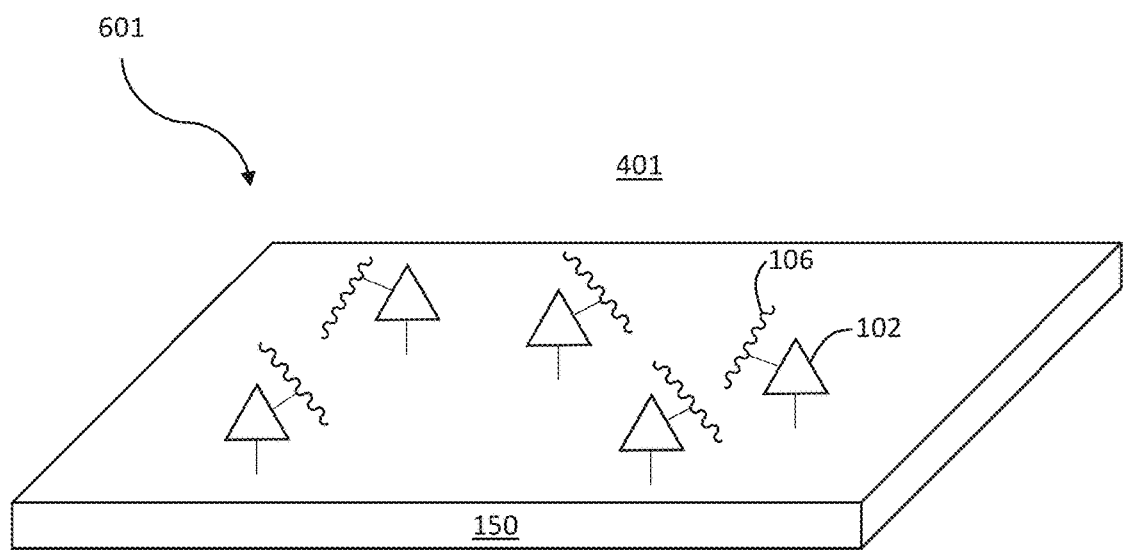
FIG. 1I is a schematic diagram of a local concentrator composite structure comprising a surface and a crystalline material in contact with a selective binding agent, according to one or more embodiments.

According to certain embodiments, the selective binding agents bound to the surface are capable of selectively binding to specific sites on a solubilized crystal precursor (e.g., a dissolved protein). FIG. 1I shows, for example, a schematic diagram of a local concentrator composite structure comprising a surface and a crystalline material in contact with a selective binding agent. As shown in FIG. 1I, composite structure 601 comprises a plurality of selective binding agents 102 bound to surface 150, wherein the plurality of selective binding agents are in contact with crystalline material 106. The plurality of selective binding agents may be bound (e.g., covalently bound) to the crystalline material, as explained herein in greater detail.

In certain embodiments, the composite structure comprising a surface may be particularly useful for generating a microneedle patch. For example, in some embodiments, the plurality of selective binding agents may selectively bind to specific sites on a solubilized crystal precursor, such as a dissolved protein or insulin, thereby providing a patch of crystalline microneedles in contact with the plurality of selective binding agents bound to the surface. After its fabrication, the microneedle patch may applied to a subject and used to deliver a drug into the subject.

Figure 2:
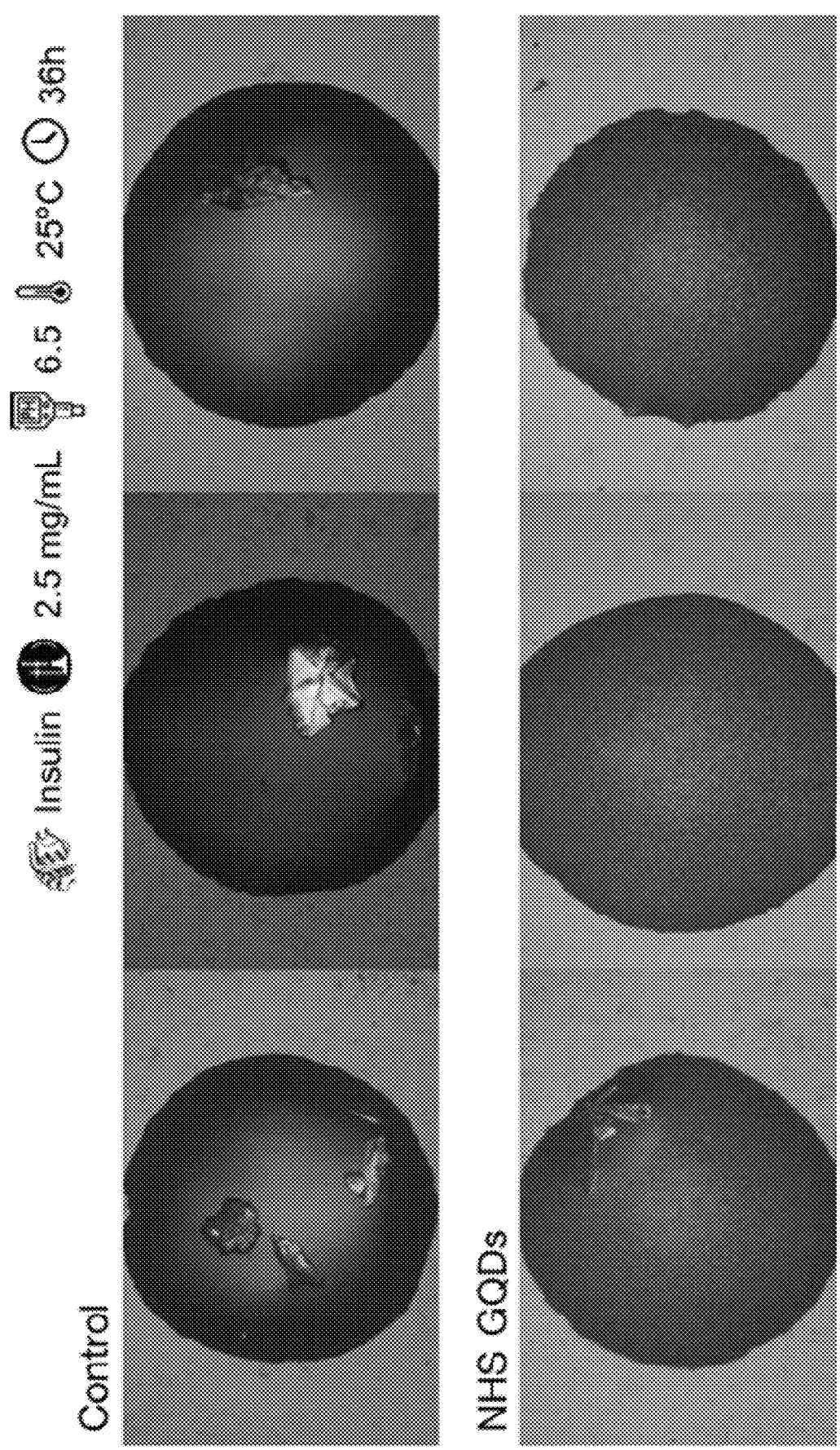
FIG. 2 shows a comparison of crystallization results of insulin for a control case in the absence of particles compared to and a case containing graphene quantum dots functionalized with N-hydroxysuccinimide ester (NHS-ester) groups, according to one or more embodiments.

FIG. 2 shows, according to some embodiments, the results of a sessile droplet crystallization screen of insulin in the presence and absence of graphene quantum dots functionalized with NHS-ester. In all 3 replicates, the control case produced a few large crystals, indicating the nucleation rate was much slower than the growth rate. Conversely, in the particle-assisted case, a large number of small crystals developed in all 3 replicates, suggesting the nucleation rate was significantly greater.

Figure 3:
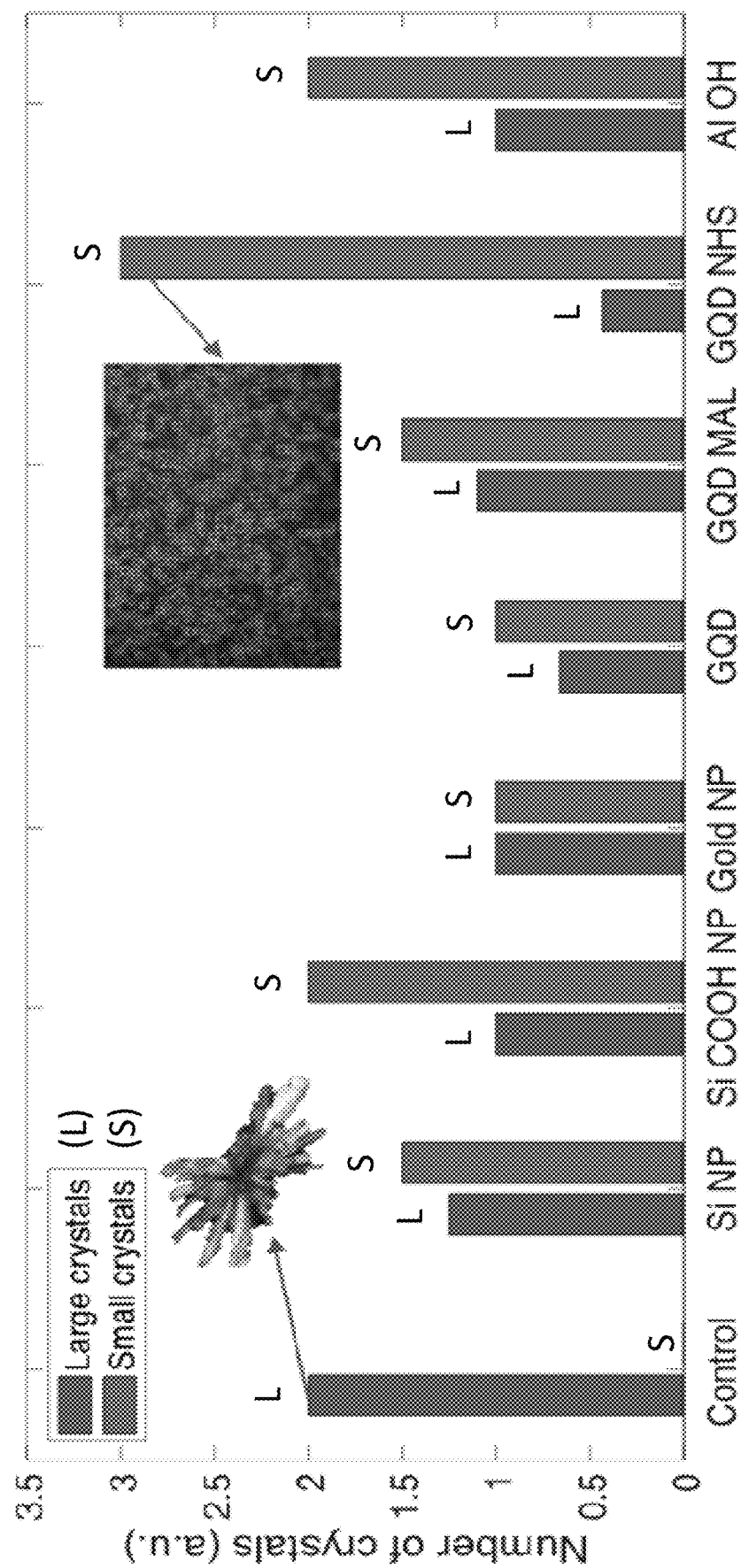
FIG. 3 shows the relative prevalence of large and small crystals for each of the particles screened in the nucleation of insulin, according to one or more embodiments.

FIG. 3 shows, according to some embodiments, the relative prevalence of large and small crystals in the case of each of the particles screened for insulin crystallization. Beyond the two cases described in FIG. 2, the other particles display intermediate ratios of small to large crystals indicating the nucleation rate can be tuned by selecting particles with the right interaction with the proteins.

Figure 4:
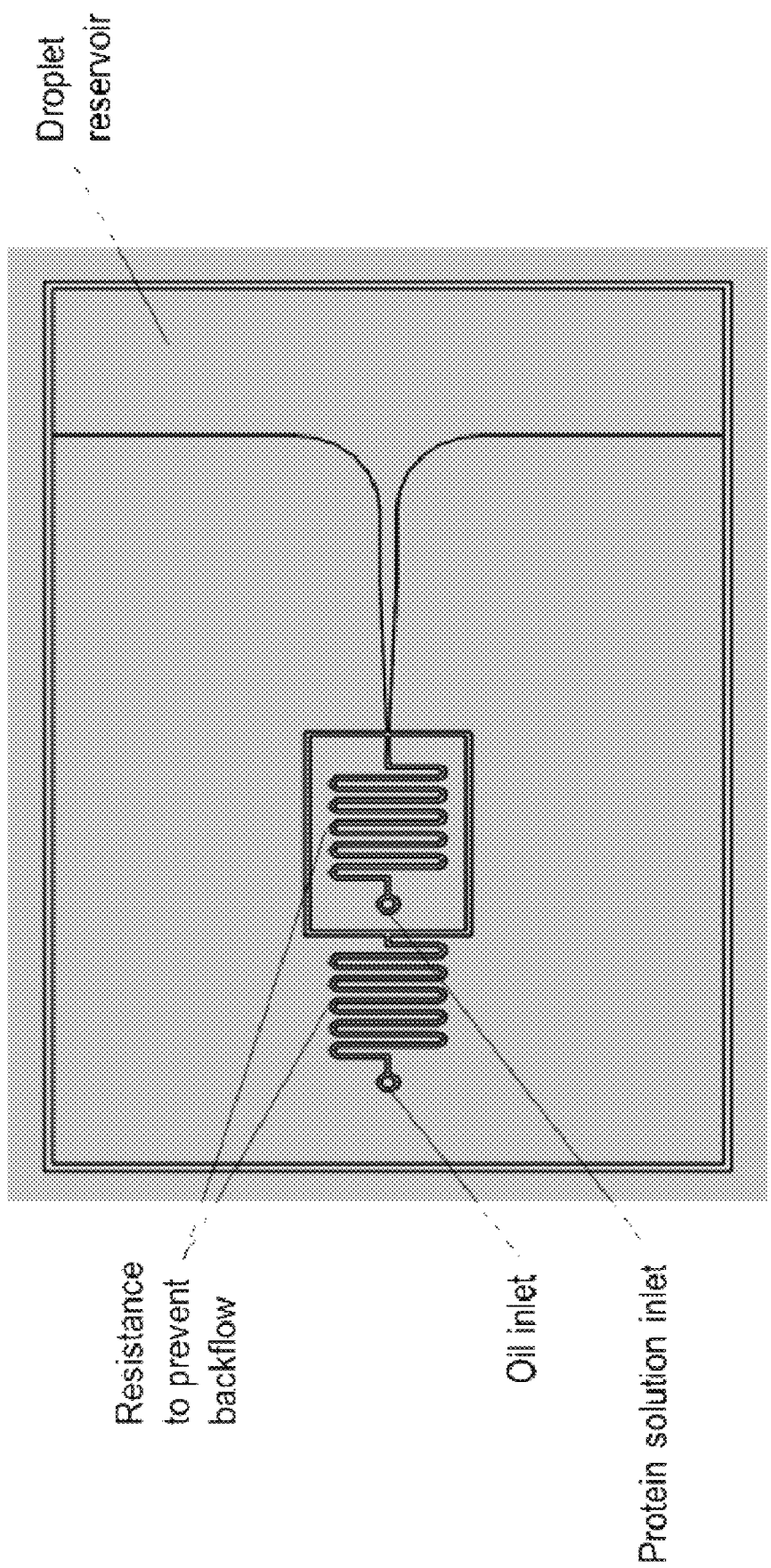
FIG. 4 shows a computer aided-design (CAD) drawing of an emulsion generator that can be used to create protein solution-in-oil solutions, according to one or more embodiments.

Emulsion-based crystallization (e.g., in an emulsion-based crystallization system) can also be used, in accordance with certain embodiments. FIG. 4 shows an emulsion generator that can be used for this purpose.

In some embodiments, the device includes ports to flow a controlled solution of particles and mix them with the protein solution. In some embodiments, the oil is selected to have low protein binding to prevent denaturation and could be further engineered by including environment responsive particles (e.g., particles that heat the solution when exposed to light) or surfactants providing specific protein interactions.

In accordance with some embodiments, a water-in-oil-in-water emulsion where the inner aqueous phase contains protein crystals has significant advantages as a drug formulation. For example, the controlled interfaces and solid state of the product suggest a high stability and longevity which could alleviate the cold-chain requirements imposed by the instability of complex drug compounds. In addition, in some cases, the oil in the emulsion can act as adjuvant in the case of vaccine formulations, suppressing the need for additional components in the product.

In certain embodiments, domains (e.g., particles, emulsions) with specific protein interaction properties can be used to influence the crystallization process and allow the tuning of the nucleation rate of crystals (e.g., protein crystal, other crystals). This fine-tuned control can be used, in accordance with certain embodiments, to produce large amounts of small crystals to be used as seed crystals in large bulk crystallizers for industrial protein crystallization or to steer the crystallization process toward fewer larger crystals for analytical purposes.

The following examples are intended to illustrate certain embodiments of the present invention, but do not exemplify the full scope of the invention.

Example 1

This example describes in situ templating to enhance protein nucleation.

Figure 5:
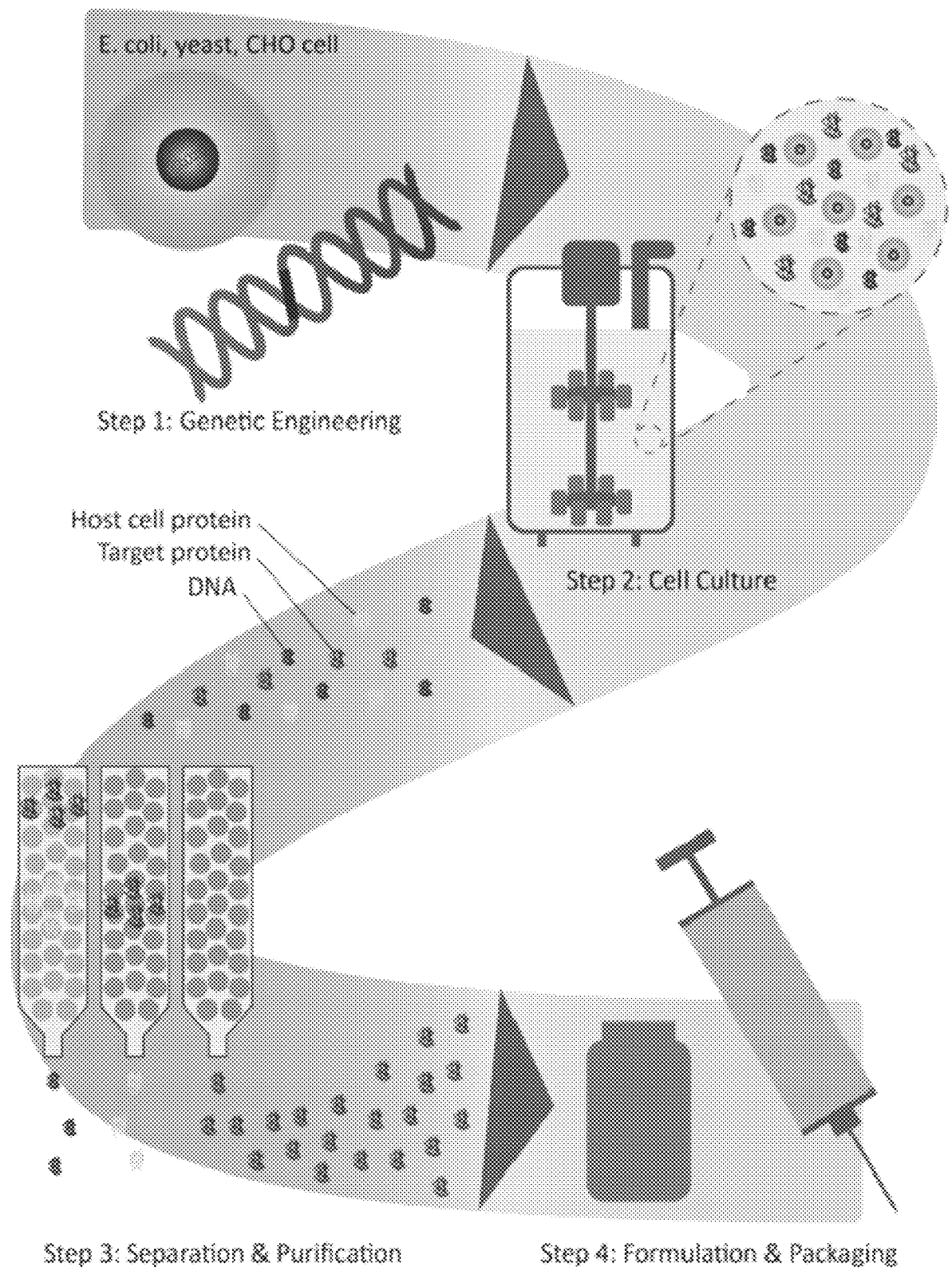
FIG. 5 shows a manufacturing process of recombinant protein-based drugs, according to one or more embodiments.

Because of their ability to target biological receptors and integrate in existing pathways, protein-based drugs have gained significant interest in the biopharmaceutical industry. They are evaluated for the treatment of cancer, cardiovascular, respiratory and infectious diseases. Monoclonal antibodies (mAbs) make up a large portion of these new therapeutic agents because of their specificity to antigens of interest. Challenges remain, however, in several areas. First, the manufacturing process of protein-based drugs, illustrated in FIG. 5, involves an extensive purification step to separate the protein of interest from host-cell proteins, nucleic acids, and cell debris present in the bioreactor. Because these components can have highly similar characteristics, separating them involves multiple stages to selectively remove, or retain, one at a time. Chromatography is traditionally used in this step and can attain a high degree of purity. However, it involves costly and specialized resins and eluents as well as tight quality control to balance the maximization of efficiency while keeping impurities at a low level. For these reasons, the separation step can account for up to 50% of the manufacturing cost of a drug. Then, a typical injection of mAbs requires large dosages of 100 mg to 1 g of protein. Because the maximum concentration of proteins in a liquid formulation is limited to around 50 mg/mL due to denaturation and aggregation, the injection volumes can reach up to 20 mL. Such volumes can only be administered intravenously in a clinical setting which increases the cost of these therapies. Finally, protein-based drugs must be carefully formulated and generally kept in cold storage to maintain acceptable biological activity. Combined with high research and development costs, the manufacturing costs of these drugs have made them inaccessible to a large portion of patients both in the developed and developing world.

To make these drugs easier to manufacture and more affordable, significant research efforts have been deployed to look for an alternative purification process. As demonstrated by the success of insulin, crystallization can be used both as a separation mechanism and as a delivery formulation. In addition to simplifying the purification by reducing the number of steps and achieving high purity, the resulting crystalline product also combines a better shelf life than formulated agents and a very high concentration, making sub-cutaneous delivery possible.

Numerous challenges, however, remain before the crystallization of proteins can be used at scale. While some proteins, like insulin, crystallize easily, most require very specific conditions in terms of pH, ionic strength, buffer, precipitants, and temperature. High-throughput testing is commonly used to narrow down promising conditions. Even in the best conditions, though, the formation of crystals can take days to weeks and require a high concentration of proteins, often in the 10 to 50 mg/mL range. These concentrations are significantly higher than those in the supernatant of a bioreactor which suggests a concentration step would be required before crystallization can be used for separation. Finally, denaturation and aggregation act as competing processes at high protein concentrations and result in loss of product before it can crystallize.

To address these challenges, the objective of this study was twofold: achieve nucleation of crystals in undersaturated conditions and increase the nucleation rate.

Figure 6A:
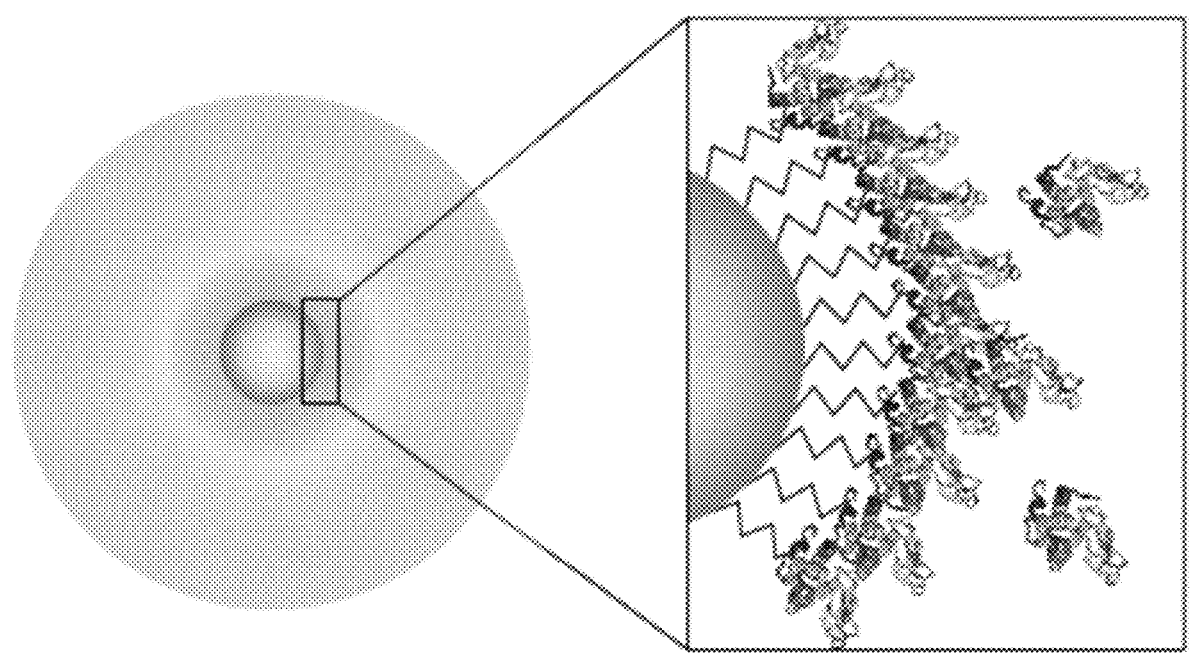
FIG. 6A shows a schematic of functionalized gold nanoparticles, according to one or more embodiments, in which the specific functionalizations are shown binding to the specific sites on proteins.
Figure 6B:
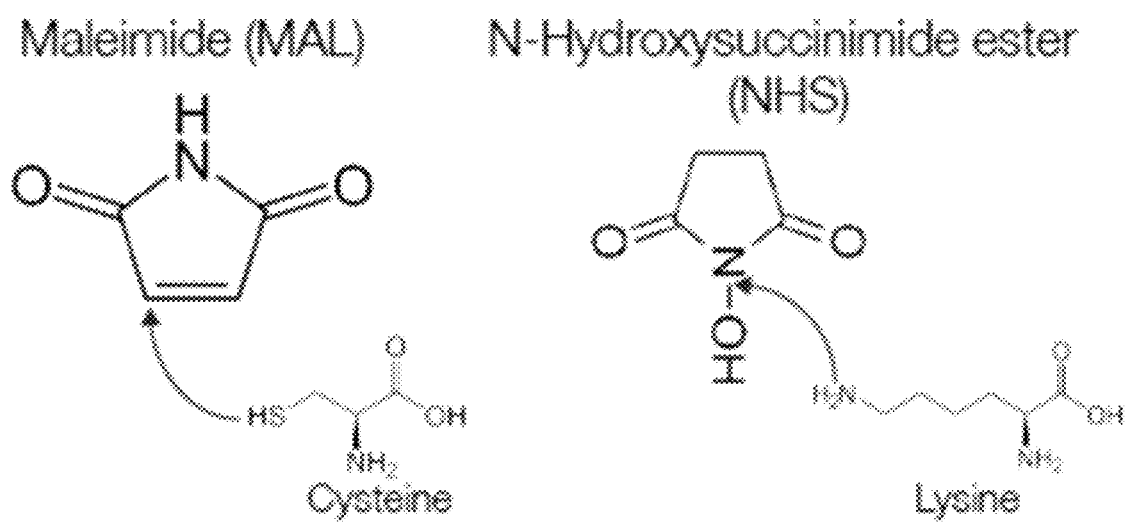
FIG. 6B shows bioconjugates used as functionalization on the nanoparticles and their respective interactions with the target amino acids, according to one or more embodiments.

In contrast to the traditional use of nanoparticles in protein crystallization that relies on adsorption or electrostatic interactions with the proteins, the approach described here aims to bind to the proteins in a specific site. FIG. 6A shows the concept schematically: a gold nanoparticle is functionalized with a group that selectively binds to specific amino acids. The proteins that come in contact with the particle end up covalently bound to it. In addition, since the individual amino acids in a protein can be more or less available and reactive, it is kinetically favored for the proteins to react on the same amino acid, thus imposing the same orientation for all proteins and forming an ordered, covalently bound template at the surface of the nanoparticle. Indeed, prior studies have found that an ordered layer of the protein to crystallize can lead to favorable molecular interactions with the solute molecules that can result in their alignment and reduce the entropic penalty of crystalline nuclei formation. In this example, the bioconjugates maleimide (MAL) and N-hydroxysuccinimide ester (NHS-ester) were chosen as the functional groups covering the gold nanoparticles (5 nm in diameter). Maleimide reacts with the thiol group present on cysteine while NHS reacts with the primary amine found on Lysine or the N-terminus of proteins as illustrated in FIG. 6B. Because only specific exposed sites on the proteins will bind to the functionalized nanoparticles, the proteins are more likely to bind in the same orientation, leading to a highly ordered layer of proteins on the nanoparticle, which could allow for crystals, which are a highly ordered arrangement of proteins, to nucleate more quickly. Other functional groups, including carboxylic groups and amine groups, on gold nanoparticle were also evaluated. On these nanoparticles, non-covalent interactions between the functional groups (or bare gold surface) and the proteins means that the proteins will be randomly oriented on the nanoparticle surface.

The 5 nm bare gold nanoparticles and gold nanoparticles functionalized with carboxylic acid and amine groups were purchased from Sigma-Aldrich, and NHS and maleimide gold nanoparticle conjugation kits were purchased from Sigma-Aldrich and prepared according to the instructions provided.

The crystallization of lysozyme (an enzyme involved in bacterial resistance that catalyzes the breakdown of certain microbial cell walls and is present in large quantities in egg white but also in tears, saliva, milk and mucus) was studied. Lysozyme was chosen because it has long been studied in the context of protein crystallization, enabling the work to start from known crystallization conditions and providing a benchmark against which to compare the results.

Figure 7A:
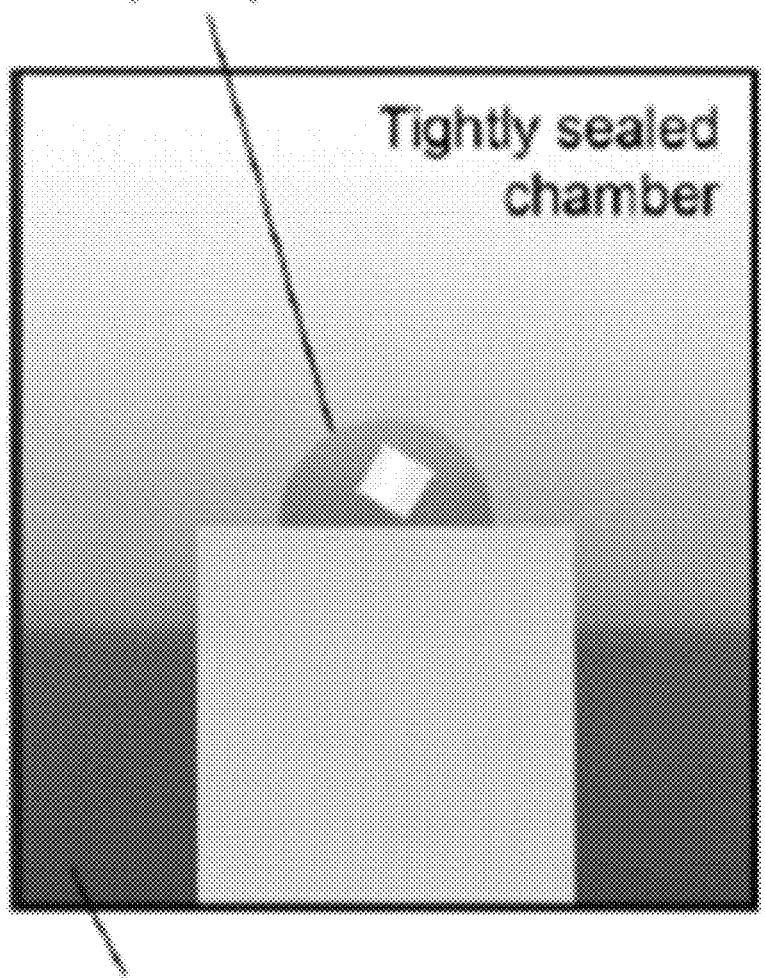
FIG. 7A shows a schematic of a vapor diffusion setup, according to one or more embodiments.

To evaluate the approach, vapor diffusion crystallization was performed. This method involved placing a droplet containing the proteins, precipitants, and particles in a sealed chamber where there was also a large reservoir of buffer at a higher salt concentration as shown schematically in FIG. 7A. Because of the difference in salt concentration, the liquid in the droplet is subject to a vapor-mediated osmotic gradient transporting it to the reservoir which lowers the amount of water in the droplet thereby increasing the concentration of protein, precipitants, and particles over time. An appropriate choice of reservoir salt concentration (2 to 10 times the concentration in the droplet) and the vapor-diffusion nature of the transport ensured the process was slow enough that it could be considered quasi-static and did not lead to the precipitation of proteins out of solution.

Figure 7B:
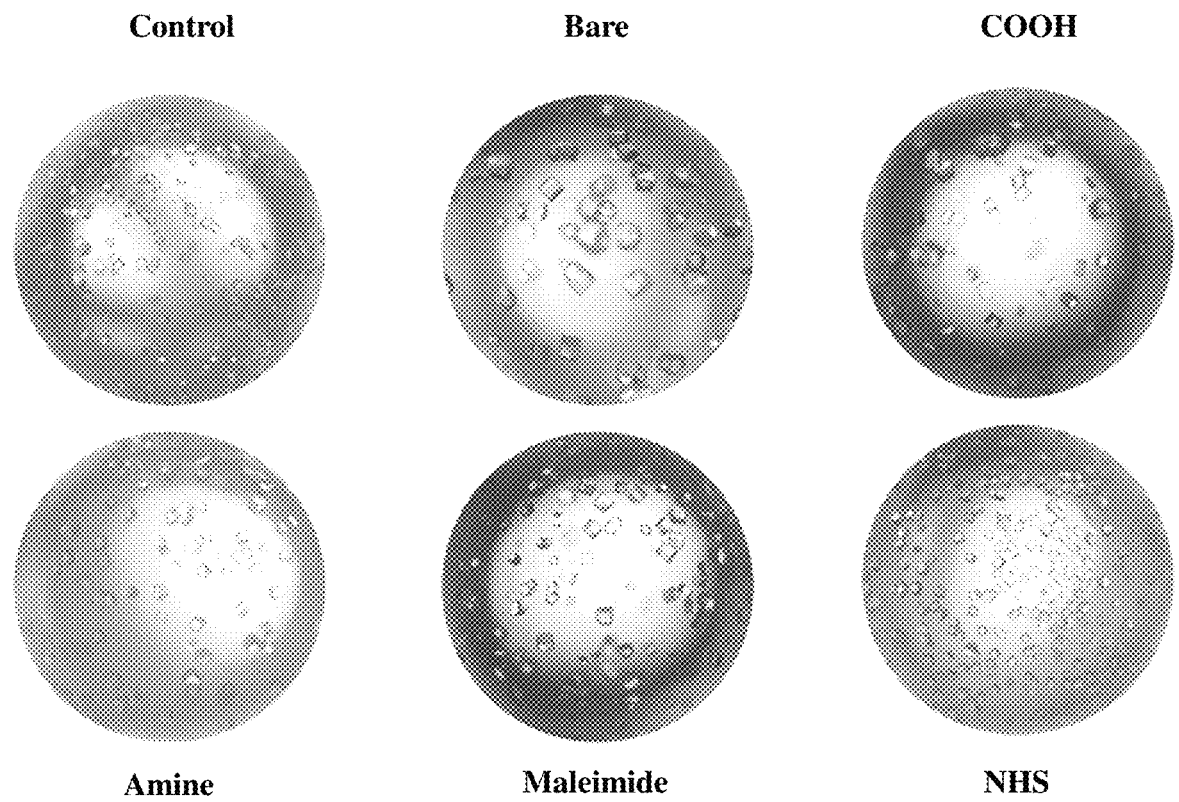
FIG. 7B shows representative droplets obtained at the end of vapor diffusion experiments for different nanoparticle functionalization, according to one or more embodiments.

A vapor diffusion experiment was chosen, starting at a lysozyme concentration of 20 mg/mL and sodium chloride concentration of 30 mg/mL in a sodium acetate buffer (50 mM) at pH 4.5. After initial preparation, the solution was split in multiple groups, each receiving the addition of 16 microliters of nanoparticles (OD 1, concentration $5 \times 10^{13}$ particles/mL) per 1 mL of solution of a specific functionalization. The resulting solutions were then used to generate 3 microliters droplets placed in a vapor diffusion chamber with a reservoir of 100 mM sodium acetate with 60 mg/mL sodium chloride. After 20 hours at room temperature, the sealed chamber was opened and the droplets were imaged with a microscope. Representative outcomes of this experiment are shown in FIG. 7B for a control in which no nanoparticles were added, bare gold nanoparticles, carboxylic acid functionalized gold nanoparticle, amine functionalized gold nanoparticles, maleimide functionalized gold nanoparticle, and NHS functionalized gold nanoparticle, respectively.

A dichotomy appeared in the results where the bare gold, amine functionalized particles, and carboxylic acid functionalized particles led to fewer, larger crystals while the NHS and maleimide functionalized particles led to more, smaller crystals. The first outcome is consistent with prior literature on the use of nanoparticles to improve crystal quality for X-ray diffraction purposes. Indeed, these studies report that the addition of nanoparticles, either bare or with various non-specific functionalizations, can result in large crystals which are favorable for use in X-ray diffraction. Conversely, these results indicate that the specific functionalizations proposed in this study lead to a different outcome, all other conditions being equal. Assuming the growth rate of the crystals is equal in all the cases, the presence of more, smaller crystals is indicative of a higher nucleation rate in the presence of nanoparticles functionalized with bioconjugates.

While these results were promising, vapor diffusion experiments did not permit a quantitative study of crystallization since the final concentration in the drops is usually significantly above supersaturation to ensure crystallization happens. In addition, because the concentration of all species is constantly changing, it is difficult to pinpoint differences in the minimum concentration for nucleation. For the same reason, it is also impossible to measure a nucleation rate using this method.

Figure 8:
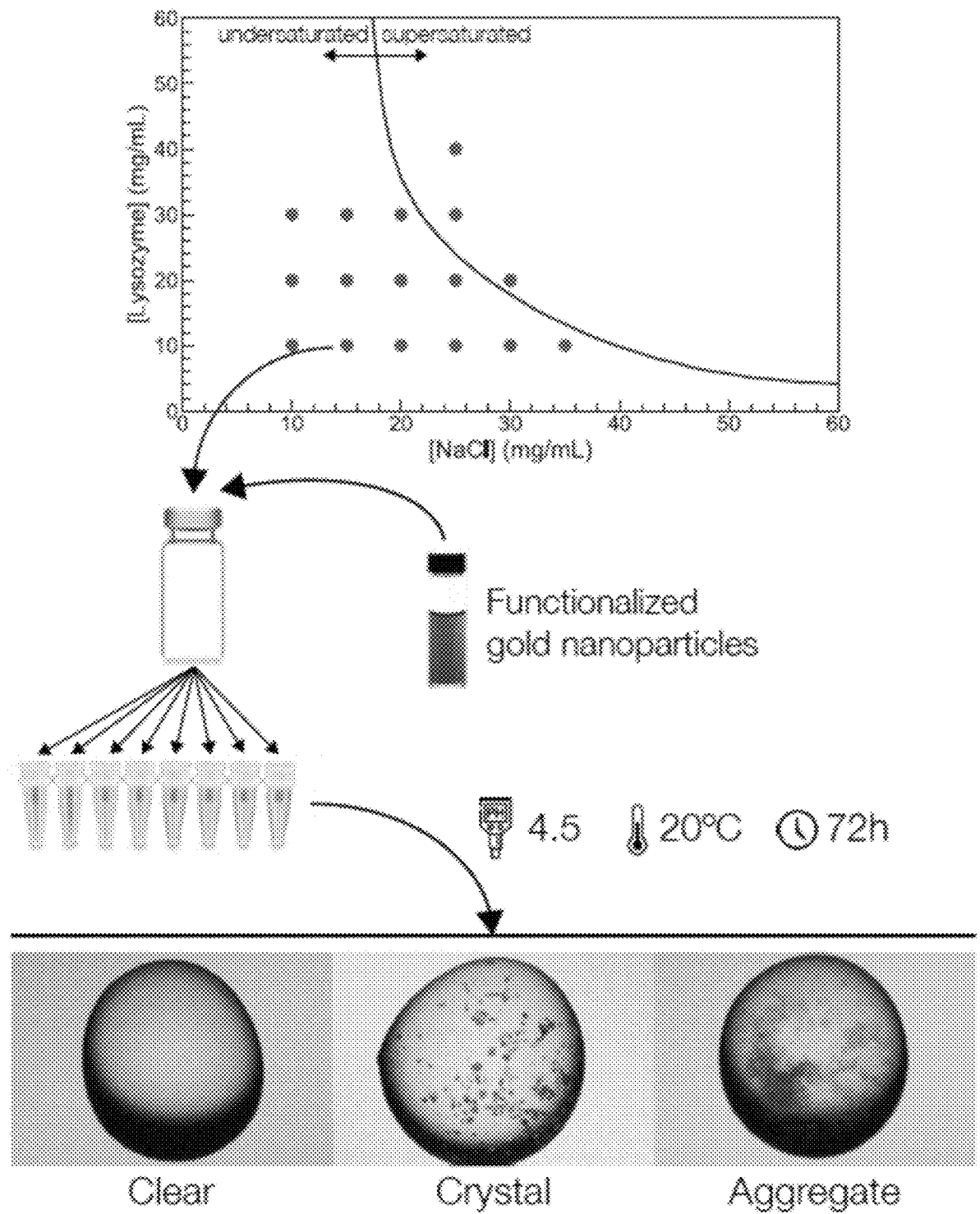
FIG. 8 shows an illustration of the investigation of undersaturated nucleation, according to one or more embodiments.

To gain a quantitative insight into the nucleation of lysozyme in undersaturated conditions, batch crystallization experiments were performed. Starting from a known solubility diagram for lysozyme as a function of sodium chloride concentration in a sodium acetate buffer (50 mM, pH 4.5) at room temperature (shown in the top section of FIG. 8), an experimental matrix was designed aiming to probe the crystallization outcome at different levels of supersaturation. The dots in FIG. 8 show the conditions that were tested. Two mother solutions were prepared, one of high lysozyme concentration (50 mg/mL) and one of high sodium chloride concentration (150 mg/mL). The lysozyme solution was filtered with a 0.2 micrometer syringe filter to remove undissolved and aggregated proteins. The solutions were then combined to achieved concentrations—and supersaturation levels—shown in FIG. 8. This method ensured that the solution reached the final saturation immediately before the addition of nanoparticles. Each condition was then further split in several 1.5 mL batches, each receiving the addition of 16 microleters of nanoparticles of different functionalization per 1 mL of solution (OD 1, concentration $5\times10^{13}$ particles/mL) except for the control case. These batches were then further divided in 8 Eppendorf tubes each (150 microliters) and left undisturbed at room temperature for 72 hours. At the end of this equilibration period, a 30 microliter droplet was withdrawn from the bottom of each tube and placed on a microscope slide for examination. The spectrum of possible outcomes is shown at the bottom of FIG. 8, which shows representative images of the droplet extracted from the crystallization tubes at the end of the experiment: the droplets could end up clear, containing crystals, or showing aggregated and precipitated protein.

Figure 9A:
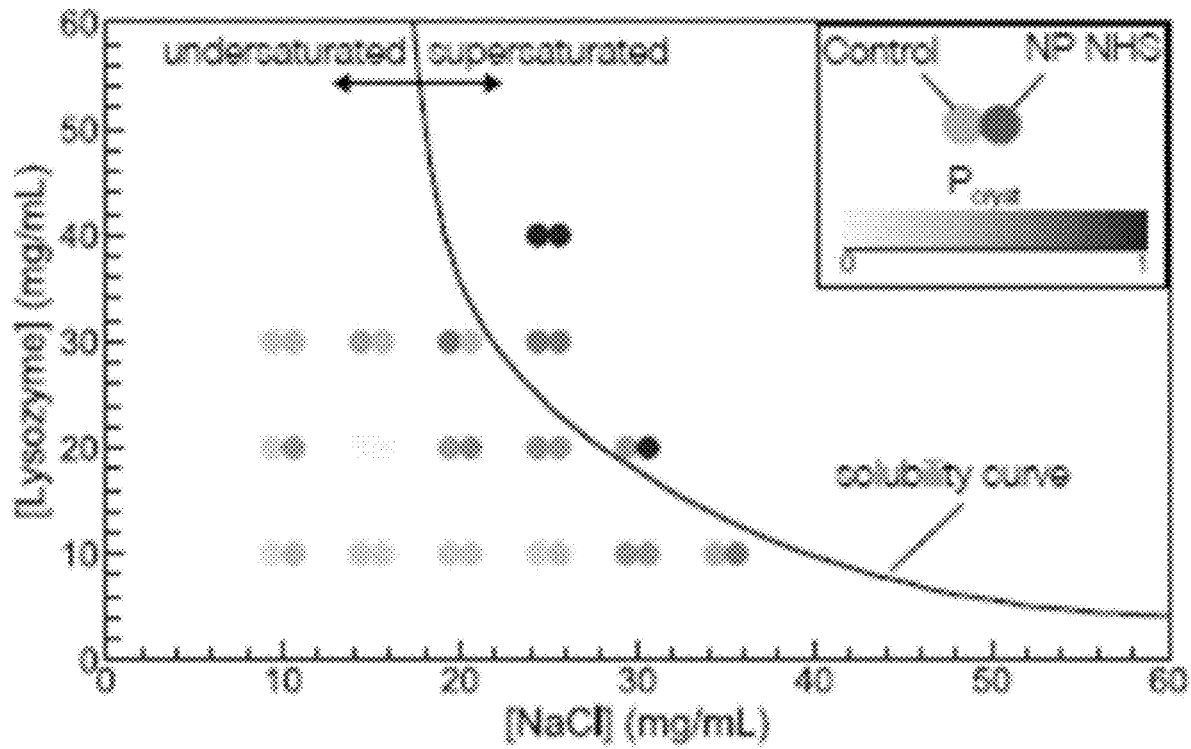
FIG. 9A shows the probability of observing crystals after 72 hours as a function of position in the solubility diagram for particle-less control and NHS functionalized nanoparticles, according to one or more embodiments.

The outcome was tabulated for each drop and allowed for the calculation of a probability of nucleation in each condition as the ratio of the number of drops exhibiting crystals to the total number of drops. Cases where a significant number of drops ended up with precipitated proteins were deemed too supersaturated and left out of the analysis. The results for the NHS functionalization are shown in FIG. 9A. For each condition, two dots are shown. The leftmost represents the probability of crystallization in a control case—without nanoparticles—while the rightmost represents the case where nanoparticles were added. In cases of high supersaturation, the probability of observing crystals was high in both cases ([Lyz]=40 mg/mL, [NaCL]=25 mg/mL for instance) as expected. More interestingly, in cases where the supersaturation was low, the presence of nanoparticles appeared to increase the nucleation probability by up to 30 percentage points. These results suggest that the nanoparticles enable undersaturated nucleation.

Figure 9B:
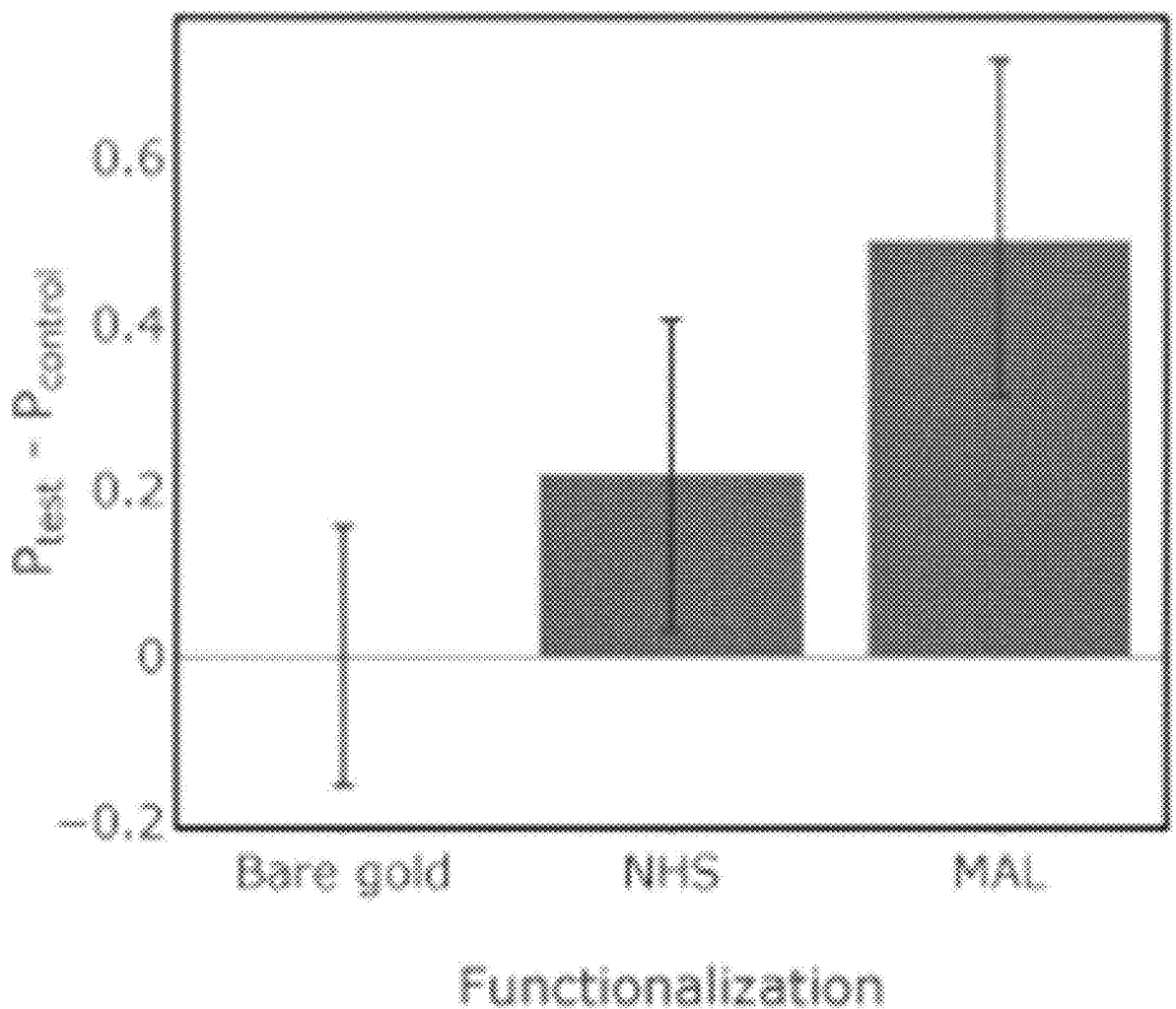
FIG. 9B shows an increase in crystallization probability relative to particle-less control as a function of functionalization used on the particles.

Focusing on the industry-relevant case of low protein concentration, an undersaturated case was selected for further study ([Lyz]=10 mg/mL, [NaCL]=35 mg/mL). A similar batch crystallization experiment was repeated with 32 replicates to gain better confidence. The results of this experiment are shown in FIG. 9B where each bar represents the difference between the nucleation probability in the test case—with nanoparticles—and in the control case—without nanoparticles. In each case, the error bars represent a 95% confidence interval obtained by bootstrapping from the experimental sample. The results indicate that, while bare nanoparticles did not have a significant effect on nucleation probability, the presence of NHS and MAL functionalized particles increased the nucleation probability by 20 and 50 percentage points respectively.

These results demonstrate the use of in situ templating to enable nucleation in solutions that would otherwise be undersaturated.

Because protein crystal nucleation is a stochastic phenomenon, population statistics need to be measured to derive the nucleation rate. Experimentally, an emulsion-based technique will be used that relies on the generation of a large number of identical but independent droplets, each containing the protein of interest, precipitants, and in the test cases, nanoparticles. Emulsion-based techniques enable control over protein and precipitant mixing and allows the crystallization progress to be monitored at time internals.

Indeed, given a nucleation rate J at a particular supersaturation, the probability to observe crystals in a droplet of volume V, after a time t since reaching supersaturation is: $P_{crystal}$=JVt. Across a population of N identical droplets, the fraction $f_{clear}$=$N_{clear}$/N of droplets that have not nucleated is equal to the probability that a single droplet has remained clear until this time $P_{clear}$(t) and follows a typical exponential decay law such that:

$$P_{clear}=f_{clear}=e^{-JVt} \quad [1]$$

Thus, the nucleation rate can be evaluated by experimentally measuring fclear across a population of drops and fitting the linearized version of Equation 1:

$$JV_t=-\ln(f_{clear}(t)) \quad [2]$$

Figure 10A:
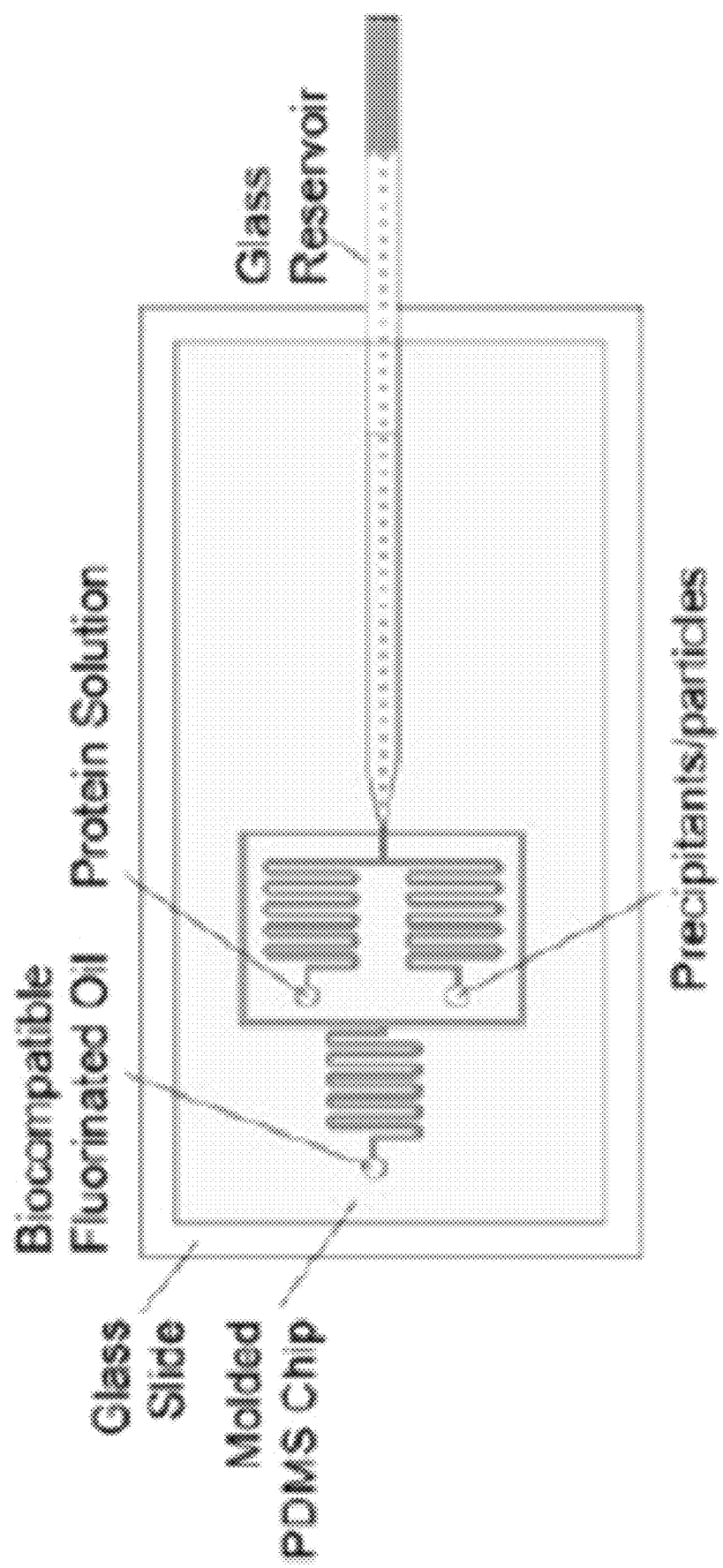
FIG. 10A shows a schematic of the microfluidic chip used to generate emulsions of identical, independent droplets containing proteins, precipitants, and nanoparticles, according to one or more embodiments.

To generate a population of identical, independent droplets, a microfluidic platform was developed combining a microfluidic mixer and an emulsion generator. A schematic of the device is shown in FIG. 10A. The two inner inlets allowed for the control and separate introduction of an undersaturated solution of proteins and the precipitant salts/nanoparticles. These streams are then mixed on-chip at a junction before the droplet generator. This process ensures that the protein solution becomes supersaturated at a controlled moment and as late as possible in its preparation. Indeed, if crystals form before the generation of the emulsion, droplets that contain seed crystals will exhibit visible crystals much faster than the ones that do not.

Figure 13A:
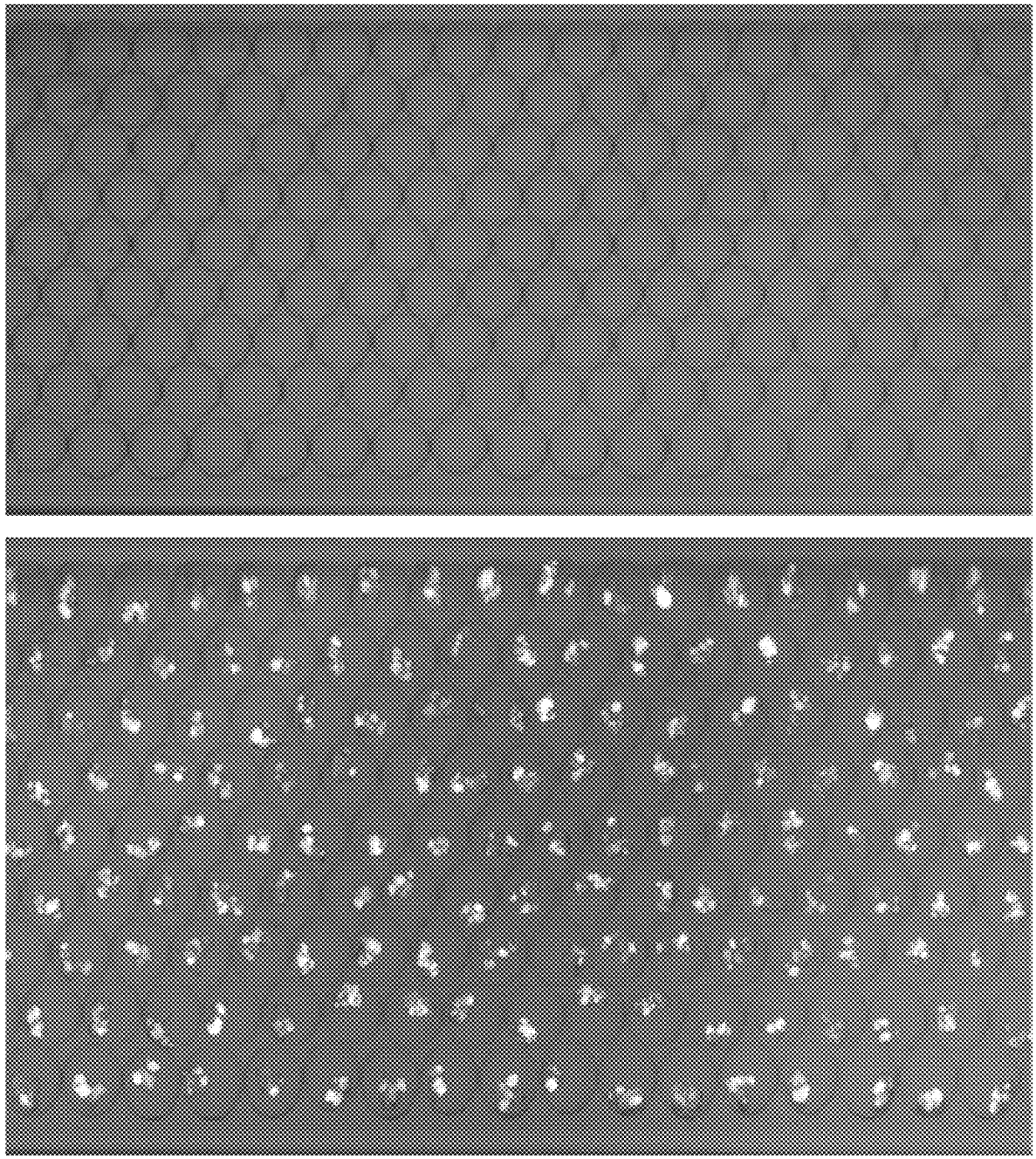
FIG. 13A shows images of an emulsion before (top) and after (bottom) crystallization, according to one or more embodiment.
Figure 13B:
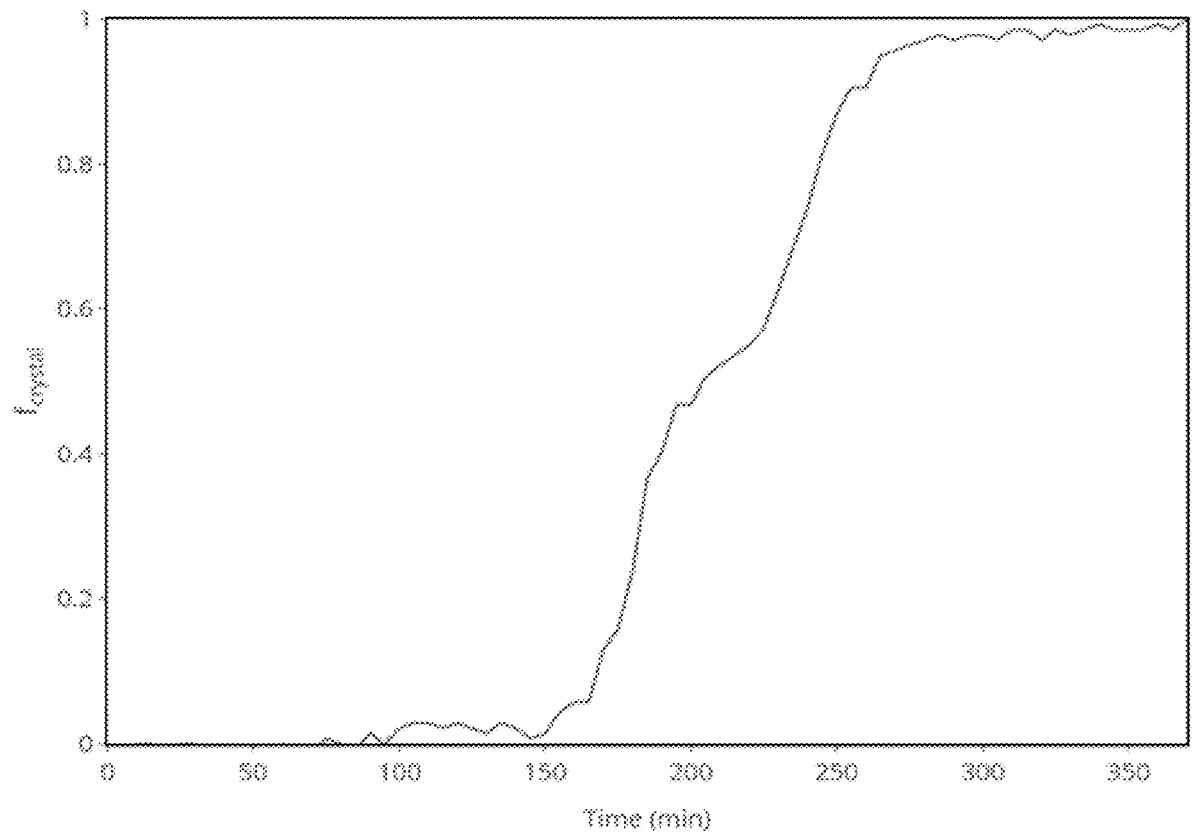
FIG. 13B shows a graph of the number of lysozyme droplets which have crystallized over time for the same experiment, according to one or more embodiments.

The next stage is a junction droplet generator that allows for the creation of identical droplets by pinching the flow of the protein solution with a flow of biocompatible fluorinated oil: HFE7500+2% 008-FluoroSurfactant (Ran Biotechnologies). Each of these inlets is connected to a pressure vessel which is in turn connected to a pressure controller (Fluigent Flow EZ). This fluorosurfactant and oil combina-tion was chosen because it did not lead to any protein denaturation, and provided stable emulsions for the duration of all experiments. The switchbacks after each inlet are flow resistance devices that help prevent backflow. The pressure of the protein and precipitant inlets are adjusted so that their flow rates are equal and the pressure of the oil inlet is increased until the transition from jetting to droplet formation. Once a stable stream of identical droplets has been generated, a thin rectangular capillary is brought in contact with the outlet of the microfluidic chip and the emulsion is drawn inside by capillary forces. The thickness of the capillary, 200 micrometers, is such that the droplets arrange in a single layer. The other dimensions 2×100 mm were chosen to facilitate imaging and maximize the number of droplets visible. The tube is then sealed with a mix of Lanolin, Vaseline, and Paraffin wax to prevent evaporation. Finally, a microscope connected to a camera is used to image the emulsion at regular time intervals—between 1 and 5 minutes. By installing two polarizers at right angle with each other along the light path before and after the capillary, protein crystals appear bright in the resulting images due to their birefringent properties. FIG. 13A shows images of an emulsion (without any nanoparticles added) before (top) and after (bottom) crystallization. FIG. 13B shows the graph of the number of lysozyme droplets which have crystallized over time for the same experiment.

Figure 10B:
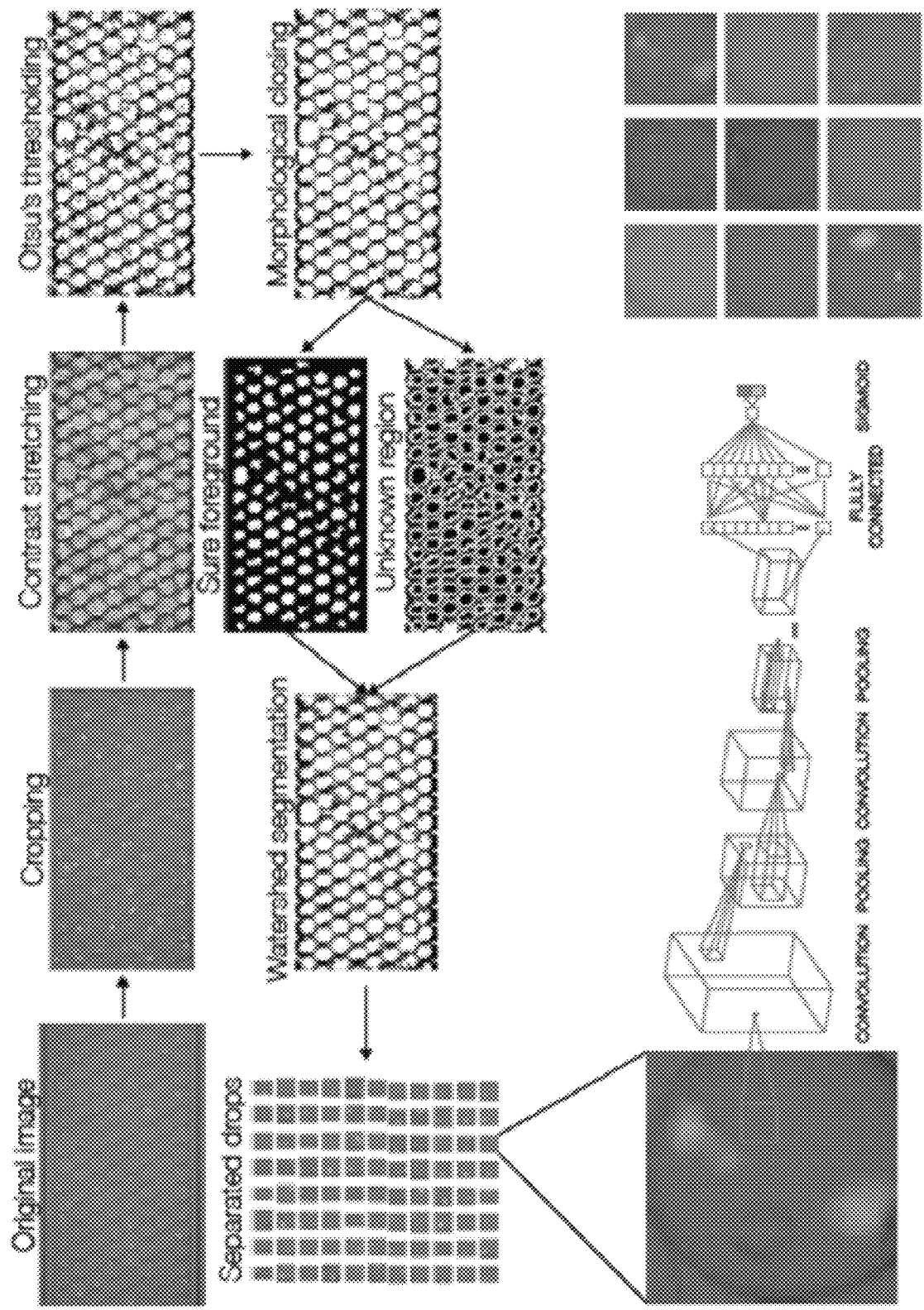
FIG. 10B shows a schematic of a segmentation pipeline used to separate droplets and a schematic of a representation of the convolutional neural network (CNN) used to classify the droplets as containing crystals or not, according to one or more embodiments.

Because of the large number of images and droplets within them, manual processing of the data in impractical. A custom software package was thus developed to segment the initial image and isolate each droplet combined with a classification algorithm to identify the presence of crystals in a given droplet. FIG. 10B shows the major steps of the segmentation algorithm. The original image is first cropped to keep only the area with droplets based on a mask provided by the user for one representative image of the experiment. A local contrast stretching algorithm is them applied to increase the contrast of the droplet contours and compensate brightness disparities due to non-uniform illumination at the edges. The resulting grayscale image is converted to a binary image by using a threshold value determined by Otsu's thresholding algorithm, which aims to minimize the intraclass variance of the intensity of the pixels assigned to the background and foreground, respectively. The resulting image generally shows a clear outline of the drops but also a number of artifacts due to the presence of the crystals. To remove these and clean up the contours, a morphological closing operation is performed where the white foreground is dilated and then contracted which smooths the outlines and erases small black spots. This is followed by an additional cleaning operation where all black continuous areas are measured and regions smaller than a specified threshold are removed. These operations result in a cleaner image where the drop outlines are well characterized. However, because of the presence of crystals at the edges of the droplets, the cleaning operations can result in multiple droplets being connected by bright pixels. This imposes the use of a segmentation algorithm that can separate these drops. First, a distance transform is applied, where the distance of each white pixel to the nearest black pixel is converted into a grayscale value. From this intermediate image, all pixels that are farther from the background than 20% of the diameter of the drop are considered sure foreground while all black pixels are considered sure background. A watershed segmentation algorithm is then applied to the morphologically closed image by using the sure foreground as seeds. This algorithm works by expending an area around each seed pixel by pixel until it meets either the background or another expanding area (originating from another seed). It then draws a boundary around each original seed corresponding to where the expansion has stopped (see FIG. 10B—Watershed segmentation). Finally, each region is analyzed to eliminate artifacts based on the circularity and total area. The remaining regions correspond to droplets that are now separated.

Once the drops are separated, the presence of crystals within each one must be determined. While this task is relatively straightforward for a person, it presents a significant coding challenge due to the different forms the crystals can adopt. Indeed, their shape can vary significantly, their size increases with time during an experiment and their brightness depends on their orientation with regards to the polarized light. Because of these challenges, a traditional classification approach based on contrast detection or histogram analysis alone did not prove sufficient to get an acceptable classification accuracy. Deep learning using a convolutional neural network (CNN) was used for this task. As shown schematically in FIG. 10B, this CNN was built from 3 convolutional layers which reduce an area the size of the specified kernel to a single value in the next layer enabling significant dimensionality reduction while retaining spatial information. Each of these layers used a square 3×3 kernel on the 150×150 input image with no striding and a rectified linear unit (ReLU) activation. Between each of these layers a MaxPooling step with a kernel size of 2×2 was used to further down-sample the input and reduce noise. A single fully connected layer was then introduced to combine the features before the output layer which used a sigmoid activation.

To train the CNN, the segmentation algorithm described above was used to generate approximately 4,000 images of individual droplets which were manually classified as either containing crystals or being clear. The training set was built to be representative of the different type of crystals that could be encountered and balanced with close to 2,000 images in each class. Once trained over 50 epochs, the model reached about 90% accuracy on both the training and validation datasets with limited overfitting. Different versions of the model with accuracies ranging from 70 to 95% (the latter obtained by overfitting a particular subset of images) were tested in the full implementation of the package and the fraction of clear droplets $f_{clear}$ was found to have very little sensitivity to the accuracy of the model over 85%.

Figure 10C:
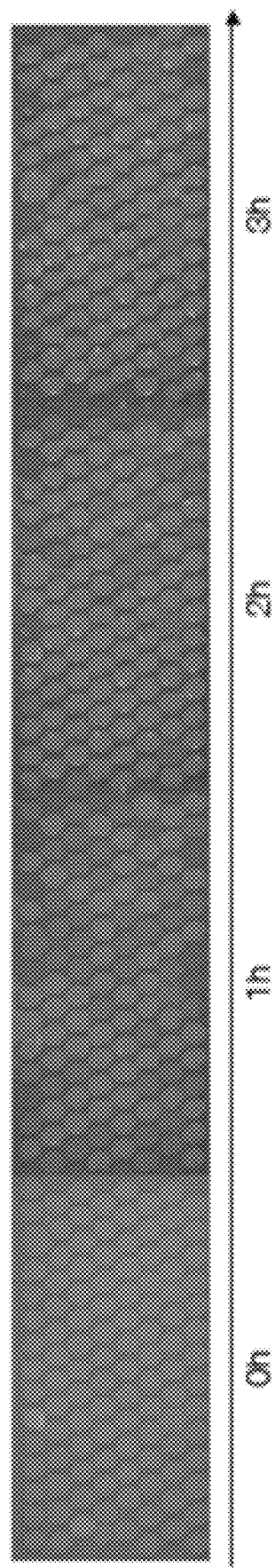
FIG. 10C shows chronophotography annotated with the contents of each droplet: clear for most cases in the left-hand image, crystals for most cases in the right-hand image, according to one or more embodiments.

The full software package described above permits the automated analysis of sequences of images of droplets. Such a time-series is shown in FIG. 10C. As time progresses, more and more drops exhibit crystals until almost all of them do after ca. 3 hours in this case. A few misclassifications in the first and last images demonstrate the level of accuracy of the classification algorithm.

Figure 11A:
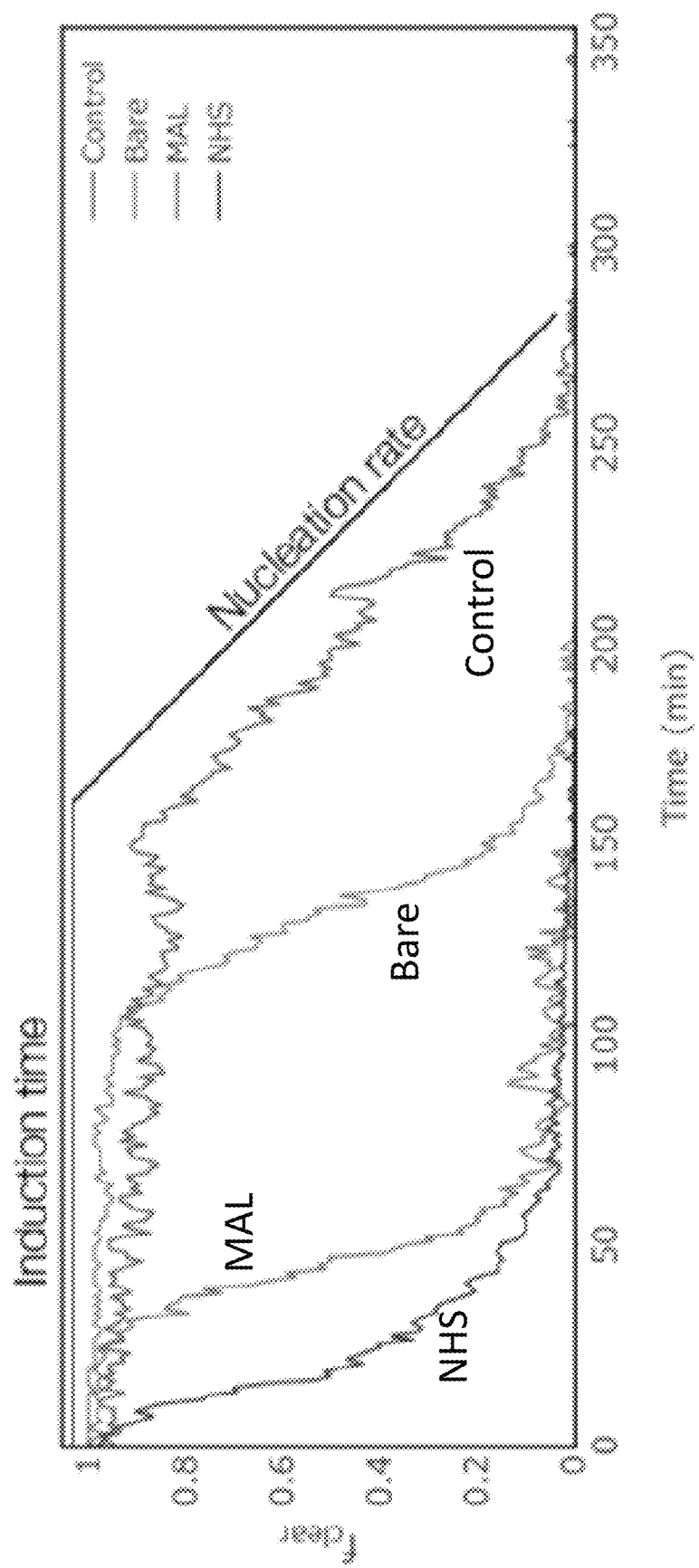
FIG. 11A shows a proportion of clear droplets in the emulsion as a function of time for different nanoparticle functionalizations, according to one or more embodiments.
Figure 11C:
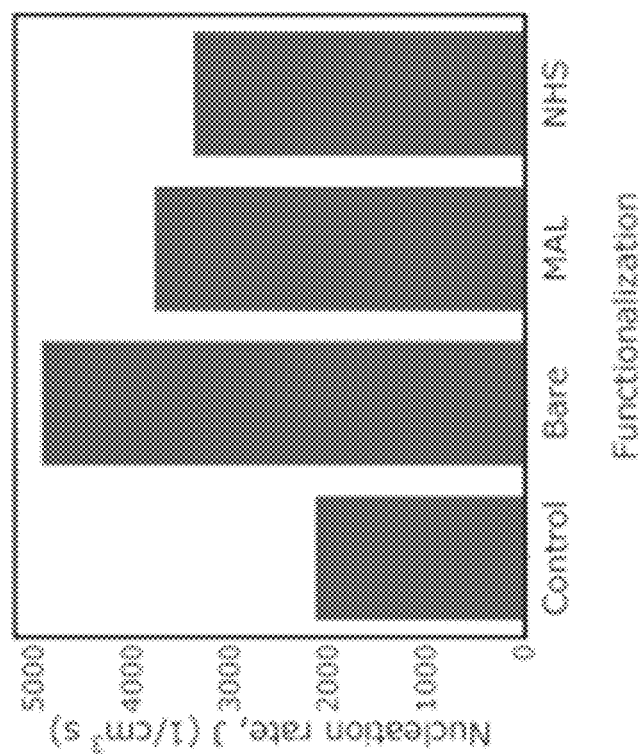
FIG. 11C shows nucleation rate as a function of functionalization, according to one or more embodiments.

To evaluate the influence of the functionalized nanoparticles on the nucleation rate of lysozyme, we ran the experiment described above with a concentration of lysozyme of 20 mg/mL and 60 mg/mL of NaCl in a sodium acetate buffer (50 mM, pH 4.5) with different nanoparticles introduced with the precipitant stream. FIG. 11A shows the fraction of clear droplets fclear as a function of time obtained by processing the series of images taken along the experiments. Two major properties of the crystallization process can be derived from these graphs: the induction time, which refers to the delay between the onset of supersaturation and the visible appearance of crystals, and the nucleation rate, derived from fitting the exponential decay portion of the curve. Qualitatively, the control case—without nanoparticles—takes longer before crystals appear and exhibits a shallower slope than the cases using functionalized nanoparticles.

Figure 11B:
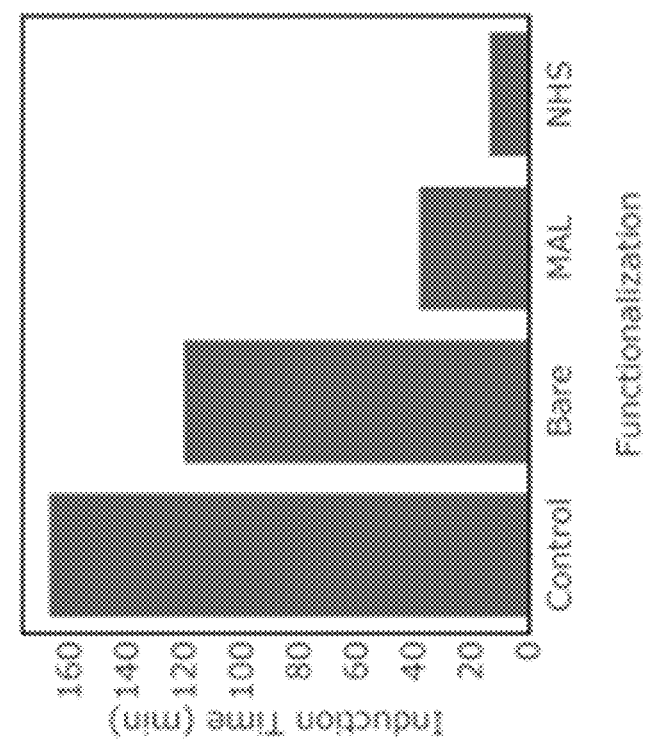
FIG. 11B shows induction time as a function of functionalization, according to one or more embodiments.

The induction time is quantitatively extracted from the previous graph by evaluating the time at which 10% of the drops exhibit crystals. This threshold provides an allowance for the accuracy of the classification algorithm while remaining as close as possible to the first observable crystals. FIG. 11B shows the extracted induction times for the different functionalizations and confirms that the presence of the functionalized nanoparticles reduced this time significantly—up to a factor of 10—compared to the particle-less control. Interestingly, the presence of bare gold nanoparticles did not decrease the induction time significantly confirming that the use of bioconjugates as functionalizations acts beyond the simple addition of heterogeneous nucleation sites.

The nucleation rate of the lysozyme crystals was derived by fitting a linearized version of the exponential decay portion of the data shown in FIG. 11A. The control case led to the smallest nucleation rate of 2,000 1/cm$^3$ s while the presence of the nanoparticles increased the nucleation by 50-100%. Interestingly the bare nanoparticles led to the highest nucleation rate despite a relatively long induction time. This could mean that the growth rate in this case was lower than in the other cases. Overall, bioconjugate-functionalized nanoparticles exhibited the optimal combination of low induction time and high nucleation rate both of which are important in the context of protein manufacturing to reduce the time it takes to crystallize the product of interest for separation.

Figure 12:
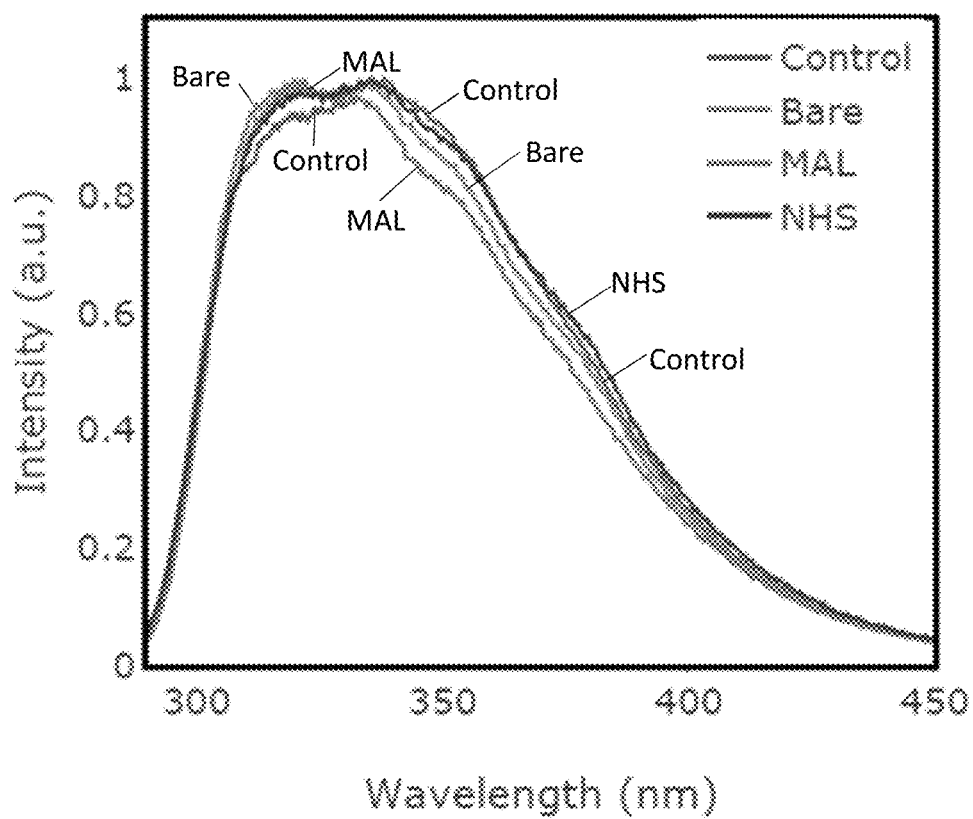
FIG. 12 shows fluorescence spectroscopy spectrum of redissolved lysozyme crystals formed in the presence of different nanoparticles, according to one or more embodiments.

To ensure that crystallization on nanoparticles did not adversely affect the shape and functionality of the proteins, a fluorescence spectroscopy analysis of the product was conducted. The crystals were collected by vacuum filtration over a PTFE membrane and rinsed them with cold (3° C.) acetate buffer to remove uncrystallized proteins. The crystals were then scrapped from the membrane with a razor blade and redissolved in 1 mL of sodium acetate buffer (50 mM, pH 4.5). The resulting concentration of lysozyme was approximately 0.1 mg/mL. A fluorescence spectrophotometer (VARIAN Cary Eclipse) was used to measure the fluorescence spectrum of the solution at an excitation wavelength $\lambda_{excit}$=280 nm (5 nm slit) between 290 and 450 nm (10 nm slit). Because of the low concentration of the solution, the highest excitation voltage (800V) and the slowest scan speed (30 nm per minute) were used to optimize the signal. The resulting spectra of fluorescence intensity were rescaled by their maximum value to account for concentration differences between the samples. The resulting data, shown in FIG. 12, exhibit a good agreement between the spectra with a peak around 330 nm consistent with the literature. Referring to FIG. 12, excitation was at 280 nm and emission was between 290 nm and 450 nm. This suggests that the redissolved proteins have kept their original morphology and, presumably, their biological activity.

This study of the crystallization of lysozyme in the presence of bioconjugate-functionalized nanoparticles has demonstrated that the latter interact with the proteins differently than nanoparticles functionalized with non-specific groups. In fact, they led to more, smaller crystals in supersaturated conditions suggesting an increase in nucleation rate. Their ability to increase the probability of crystal nucleation in undersaturated conditions suggests that they indeed act as templates for nucleation. A quantitative investigation of the nucleation rate of lysozyme demonstrated that the functionalized nanoparticles reduced the induction time for crystal formation by up to 10× and increased the nucleation rate by up to 2× in otherwise identical conditions. These promising results bring us closer to the viability of protein crystallization as a purification method or as a final formulation enabling high concentration sub-cutaneous injection.

For the vapor diffusion experiments, lyophilized lysozyme (Sigma-Aldrich) was dissolved in 50 mM acetate buffer at pH 4. The lysozyme concentration in the mother liquor was 20 mg/mL, along with 3% NaCl. The reservoir solution was acetate buffer with 6% NaCl in 100 mM acetate buffer. The gold nanoparticles in 1 OD aqueous solutions were added to the mother liquor solutions at a concentration of 15 microliters/mL and mixed before pipetting onto sitting drop crystallization trays (Sigma-Aldrich). The drops were 3 micrometers and were equilibrated against 100 microliter reservoirs. The trays were sealed and the vapor diffusion experiments run for 20 hours at 25° C., after which they were imaged with a Nikon D300 Digital SLR camera under polarized light.

The design for the microfluidic chips was created using SolidWorks 2017. The design was saved as a DXF file, and printed as a transparency mask (CAD/Art Services Inc). Preparation of an SU8 mold was done according to the following protocol: Using SU8 2150 (MicroChem), a 400 micrometer thick layer was deposited on a 4 inch wafer by spinning at 1600 rpm for 30 seconds. The wafer was prebaked for 10 minutes at 65° C. and then 90 minutes at 95° C. A blank mask was attached directly on top of the coated wafer. The mask was exposed for 80 seconds in the hard contact setting. The mask was postbaked for 5 minutes at 65° C., then 25 minutes at 95° C., then cooled completely. The mask was developed with PGMEA on spinner, then rinsed with isopropyl alcohol and dried with nitrogen.

The mold was then used to produce PDMS devices. Fabrication of PDMS microfluidic chips was done as follows: PDMS was prepared by mixing 10 parts elastomer with 1 part curing agent of Sylgard 184 (Dow). PDMS was poured over the SU8 molds, and degassed for 1 hour. The PDMS was cured for 2 hours at 75° C. The PDMS was peeled off the SU8 molds, and trimed to ensure flat, even edges. A 17G blunt tip needle (McMaster-Carr) was used to punch holes for the 3 tubing connections on each chip. The PDMS chips and 75 mm×50 mm glass slides were cleaned with plasma for 2 minutes, then bonded together by gently pressing the peeled side of the PDMS evenly onto the glass slide. In order to make the channels hydrophobic, a syringe pump was used to flow Aquapel through the channels for 1 minute, then the Aquapel was expelled with air. HFE7500 was flowed through the channels for 1 minute, then all the remaining liquid was expelled with air. The inlet holes were sized to allow the tubing (OD: 0.056") to be inserted directly into the chip.

The microfluidic chip was designed to form equal-sized droplets ranging from about 50-400 micrometers in size containing equal volumes of the protein solution and precipitant solution. A line between the two streams occurs halfway through the channel, which provides visual confirmation that the volumes of both solutions are equal.

A Fluigent Flow-EZ microfluidic pressure pump was used to control the fluid flow through the microfluidic chip. The pressures applied to each fluid were carefully controlled to sure that the appropriate sized droplets were generated. The typical pressures applied to the fluids were as follows: HFE 7500 at 75 mbar; lysozyme solution at 20 mbar; and precipitant solution at 20 mbar. Adjusting the pressure applied to the oil phase enables the size of the emulsion droplets produced to be easily tuned to the desired size.

The lysozyme solution was prepared by dissolving lyophilized lysozyme (Sigma-Aldrich) into 50 mM acetate buffer at pH 4. The solution was passed through a 0.2 micrometer syringe filter to remove any aggregates. The protein solution was then analyzed using a NanoDrop One to check the protein concentration. A concentration of 40 mg/mL was used for the nucleation experiments. The different nucleation agents—bare and functionalized 5 nm gold nanoparticles in 1 OD aqueous solutions—were added to solutions of 12% NaCl. The concentrations of protein and salts used in the emulsion generation were doubled so that the final concentrations in the droplets would be the desired 20 mg/mL lysozyme and 6% NaCl. These crystallization conditions were based on the conditions typically used for lysozyme crystallization. The salt concentration used in the nucleation experiments was experimentally determined to ensure that crystallization would occur in this experimental setup over a period of less than 6 hours.

The prepared protein and solutions were loaded into 50 mL centrifuge tubes and connected to the Fluigent pressure controller. The emulsions were generated on the chip, as previously described, and then loaded into 2 mm×200 micrometer×50 mm glass capillaries (VitroCom) which were inserted into the outlet of the chip. The emulsions were generated at a high enough volume ratio to completely fill the capillary tubes in a single layer of droplets. The capillaries were then removed from the chip and placed in a custom designed capillary holder (3D printed with the Formlabs Form2). A modified version of Valap (50% Vaseline, 25% paraffin wax, and 25% lanolin) was used to seal the tubes. The capillary holder was placed under a Zeiss Axio Zoom. V16 microscope and imaged under cross-polarized light with a Nikon D300 Digital SLR camera. The droplets were imaged once per minute until crystallization was complete (defined as when every droplet contained at least one crystal).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composite structure, comprising:
   a particle; and
   a plurality of selective binding agents bound to an external surface of the particle;
   wherein:
   an areal density of the selective binding agents over the external surface of the particle is less than or equal to 100 per $nm^2$; and
   the selective binding agents are capable of selectively binding to specific sites on a protein.

2. The composite structure of claim 1, wherein the areal density of the selective binding agents over the external surface of the particle is less than or equal to 10 per $nm^2$.

3. The composite structure of claim 1, wherein the composite structure is located within a liquid medium.

4. The composite structure of claim 1, wherein the selective binding agents are covalently bound to the particle.

5. A crystallization system, comprising:
a liquid medium comprising a solubilized crystal precursor and a plurality of particles functionalized with one or more agents;
wherein at least one of the one or more agents is configured to selectively bind to the solubilized crystal precursor;
wherein the crystallization system is capable of generating crystals comprising the solubilized crystal precursor when a concentration of the solubilized crystal precursor in the liquid medium is below a saturation concentration; and
wherein the one or more agents are capable of selectively binding to specific sites on a protein.

6. The crystallization system of claim 5, wherein an areal density of the one or more agents over an external surface of the particles is less than or equal to 100 per $nm^2$.

7. The crystallization system of claim 5, wherein the solubilized crystal precursor is a precursor of a crystallized protein.

8. The crystallization system of claim 5, wherein the one or more agents are covalently bound to the particles.

9. A method, comprising:
combining a solubilized crystal precursor with a plurality of surfaces in a liquid medium; and
generating a crystal comprising the solubilized crystal precursor;
wherein:
the solubilized crystal precursor comprises a protein, and
at least some of the surfaces comprise one or more agents configured to selectively bind to specific sites on the protein.

10. The method of claim 9, wherein an areal density of the one or more agents over the surfaces is less than or equal to 100 per $nm^2$.

11. The method of claim 9, wherein a concentration of the solubilized crystal precursor within the liquid medium is below a saturation concentration of the solubilized crystal precursor within the liquid medium.

12. The method of claim 9, wherein a concentration of the solubilized crystal precursor within the liquid medium is less than or equal to 0.9 times a saturation concentration of the solubilized crystal precursor within the liquid medium.

13. A method, comprising:
combining a solubilized crystal precursor with a plurality of surfaces in a liquid medium; and
generating a crystal comprising the solubilized crystal precursor;
wherein at least some surfaces comprise one or more agents configured to selectively bind to the solubilized crystal precursor; and
wherein at least a portion of the surfaces are part of an emulsified droplet.

14. The method of claim 13, wherein the emulsified droplet contains the one or more agents at a phase boundary of the emulsified droplet.

15. The method of claim 13, wherein the one or more agents comprise a surfactant proximate to a phase boundary of the emulsified droplet.

16. The method of claim 9, wherein at least a portion of the surfaces are surfaces of solid particles.

* * * * *